(12) United States Patent
Scirica et al.

(10) Patent No.: US 7,143,924 B2
(45) Date of Patent: *Dec. 5, 2006

(54) SURGICAL STAPLING APPARATUS WITH LOCKING MECHANISM

(75) Inventors: Paul A. Scirica, Huntington, CT (US); Stanislaw Marczyk, Stratford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/059,805

(22) Filed: Feb. 17, 2005

(65) Prior Publication Data

US 2005/0184124 A1  Aug. 25, 2005

Related U.S. Application Data

(60) Provisional application No. 60/545,619, filed on Feb. 17, 2004.

(51) Int. Cl.
*A61B 17/068* (2006.01)

(52) U.S. Cl. .............................. 227/175.2; 227/175.1; 227/175.4; 227/182.1

(58) Field of Classification Search ............ 227/175.2, 227/175.4, 176.1, 182.1, 175.1
See application file for complete search history.

(56) References Cited

U.S. PATENT DOCUMENTS

| | | | |
|---|---|---|---|
| 3,079,606 | A | 3/1963 | Bobrov et al. |
| 3,490,675 | A | 1/1970 | Green et al. |
| 3,499,591 | A | 3/1970 | Green |
| 4,244,372 | A | 1/1981 | Kapitanov et al. |
| 4,429,695 | A | 2/1984 | Green |
| 4,520,817 | A | 6/1985 | Green |
| 4,589,413 | A | 5/1986 | Malyshev et al. |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,861 | A | 1/1987 | Chow et al. |
| 4,633,874 | A | 1/1987 | Chow et al. |
| 4,672,964 | A | 6/1987 | Dee et al. |
| 4,763,669 | A | 8/1988 | Jaeger |
| 4,863,088 | A | 9/1989 | Redmond et al. |
| 4,880,015 | A | 11/1989 | Nierman |
| 4,892,244 | A | 1/1990 | Fox et al. |
| 4,978,049 | A | 12/1990 | Green |
| 4,991,764 | A | 2/1991 | Mericle |
| 5,040,715 | A | 8/1991 | Green et al. |
| 5,065,929 | A | 11/1991 | Schulze et al. |
| 5,071,052 | A | 12/1991 | Rodak et al. |
| 5,074,454 | A | 12/1991 | Peters |
| 5,083,695 | A | 1/1992 | Foslien et al. |
| 5,111,987 | A | 5/1992 | Moeinzadeh et al. |

(Continued)

FOREIGN PATENT DOCUMENTS

DE   4300307   7/1994

(Continued)

*Primary Examiner*—John Slpos
*Assistant Examiner*—Michelle Lopez

(57) ABSTRACT

The present disclosure provides for a loading unit for use with a surgical stapling apparatus. The loading unit includes a housing portion having a distal end and a proximal end, a drive assembly slidably supported within the housing portion of the loading unit, and a locking member supported on the housing portion of the loading unit. The locking member is movable from a first position wherein the locking member engages the drive assembly and maintains the drive assembly in a ready-to-load position to a second position wherein the locking member permits movement of the drive assembly relative to the housing portion.

20 Claims, 19 Drawing Sheets

U.S. PATENT DOCUMENTS

| | | | |
|---|---|---|---|
| 5,129,570 | A | 7/1992 | Schulze et al. |
| 5,141,144 | A | 8/1992 | Foslien et al. |
| 5,152,279 | A | 10/1992 | Wilk |
| 5,209,747 | A | 5/1993 | Knoepfler |
| RE34,519 | E | 1/1994 | Fox et al. |
| 5,275,608 | A | 1/1994 | Forman et al. |
| 5,282,826 | A | 2/1994 | Quadri |
| 5,307,976 | A | 5/1994 | Olson et al. |
| 5,312,023 | A | 5/1994 | Green et al. |
| 5,318,221 | A | 6/1994 | Green et al. |
| 5,326,013 | A | 7/1994 | Green et al. |
| 5,330,502 | A | 7/1994 | Hassler et al. |
| 5,332,142 | A | 7/1994 | Robinson et al. |
| 5,350,391 | A | 9/1994 | Iacovelli |
| 5,354,311 | A | 10/1994 | Kambin et al. |
| 5,374,277 | A | 12/1994 | Hassler |
| 5,376,095 | A | 12/1994 | Ortiz |
| 5,383,888 | A | 1/1995 | Zvenyatsky et al. |
| 5,397,046 | A | 3/1995 | Savage et al. |
| 5,415,334 | A | 5/1995 | Williamson, IV et al. |
| 5,415,335 | A | 5/1995 | Knodel, Jr. |
| 5,433,721 | A | 7/1995 | Hooven et al. |
| 5,465,895 | A | 11/1995 | Knodel et al. |
| 5,467,911 | A | 11/1995 | Tsuruta et al. |
| 5,474,566 | A | 12/1995 | Alesi et al. |
| 5,474,571 | A | 12/1995 | Lang |
| 5,484,451 | A | 1/1996 | Akopov et al. |
| 5,486,185 | A | 1/1996 | Freitas et al. |
| 5,487,500 | A | 1/1996 | Knodel et al. |
| 5,507,426 | A | 4/1996 | Young et al. |
| 5,535,935 | A | 7/1996 | Vidal et al. |
| 5,582,617 | A | 12/1996 | Klieman et al. |
| 5,584,425 | A * | 12/1996 | Savage et al. ............ 227/175.2 |
| 5,605,272 | A | 2/1997 | Witt et al. |
| 5,630,539 | A | 5/1997 | Plyley et al. |
| 5,634,584 | A | 6/1997 | Okorocha et al. |
| 5,762,255 | A | 6/1998 | Chrisman et al. |
| 5,797,537 | A | 8/1998 | Oberlin et al. |
| 5,820,009 | A | 10/1998 | Melling et al. |
| 5,901,895 | A | 5/1999 | Heaton et al. |
| 6,010,054 | A | 1/2000 | Johnson et al. |
| 6,032,849 | A | 3/2000 | Mastri et al. |
| 6,109,500 | A * | 8/2000 | Alli et al. ................. 227/175.2 |
| 6,241,139 | B1 | 6/2001 | Milliman et al. |
| 6,669,073 | B1 * | 12/2003 | Milliman et al. ......... 227/175.2 |
| 2005/0184123 | A1 * | 8/2005 | Scirica ..................... 227/176.1 |
| 2005/0184125 | A1 * | 8/2005 | Marczyk .................. 227/176.1 |

FOREIGN PATENT DOCUMENTS

| | | |
|---|---|---|
| EP | 0484677 | 5/1992 |
| EP | 0589306 | 3/1994 |
| EP | 0591948 | 4/1994 |
| EP | 0592243 | 4/1994 |
| EP | 0621009 | 10/1994 |
| EP | 0656188 | 6/1995 |
| FR | 2681775 | 10/1991 |

* cited by examiner

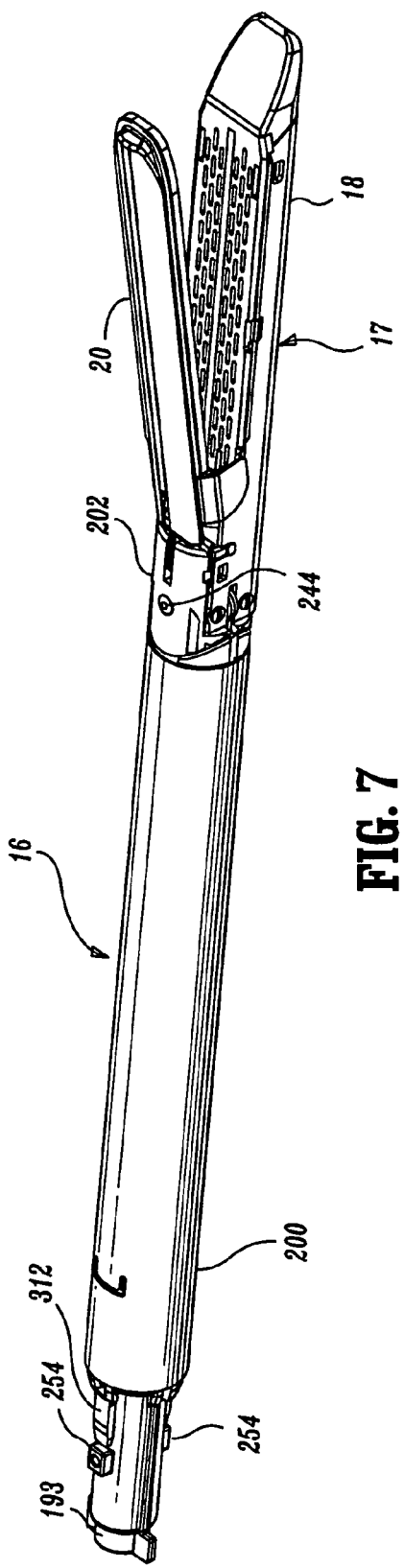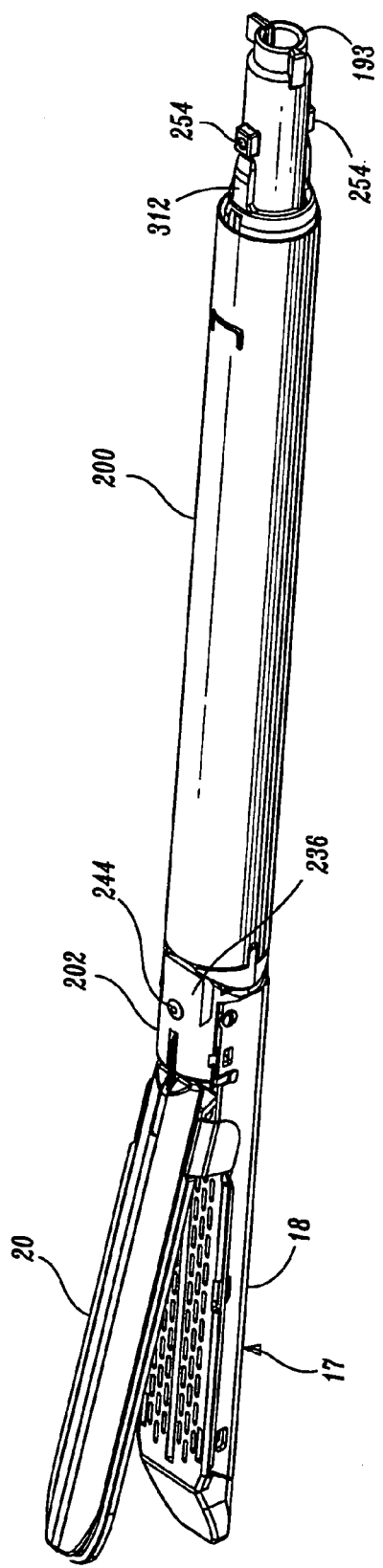

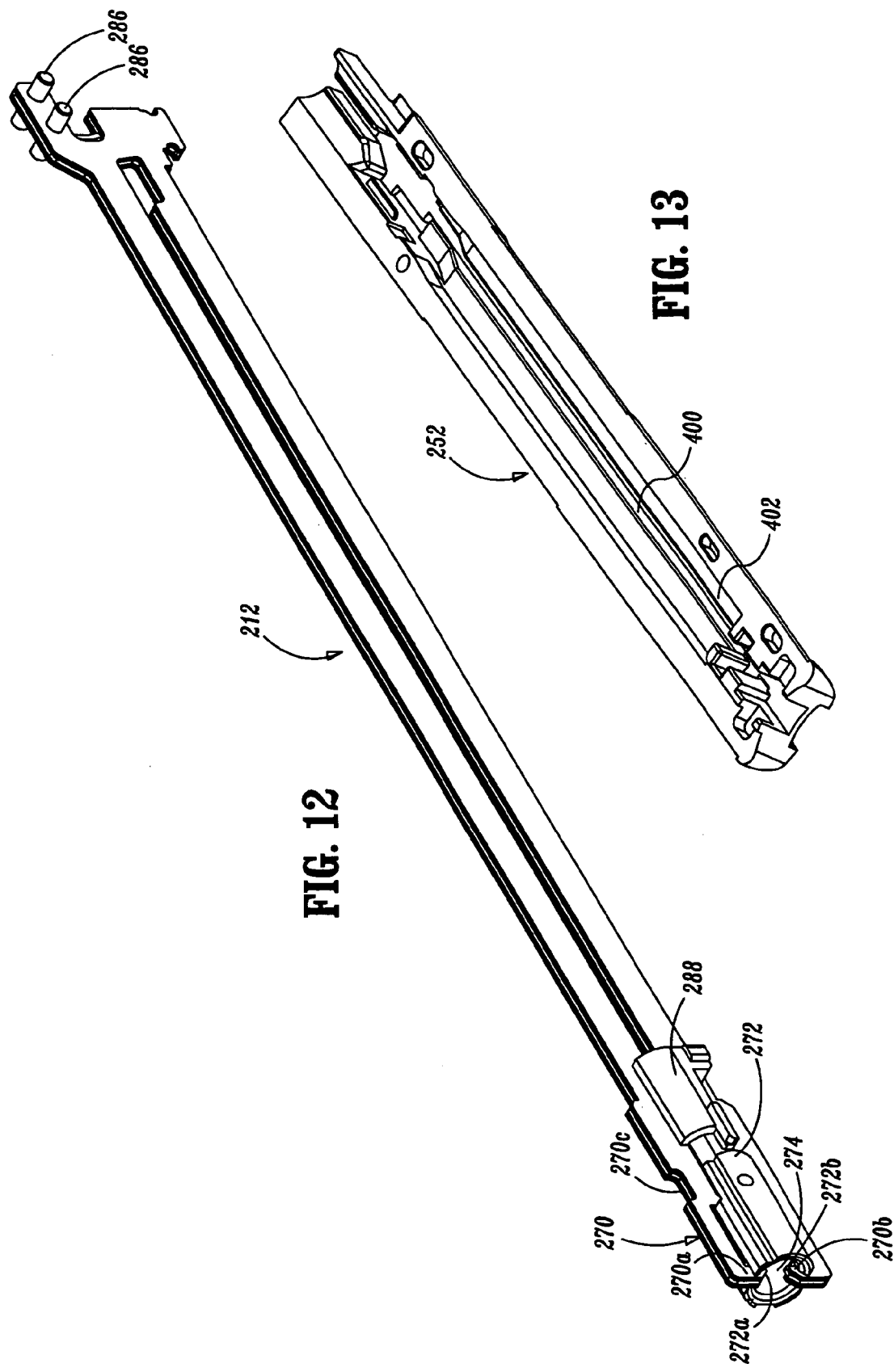

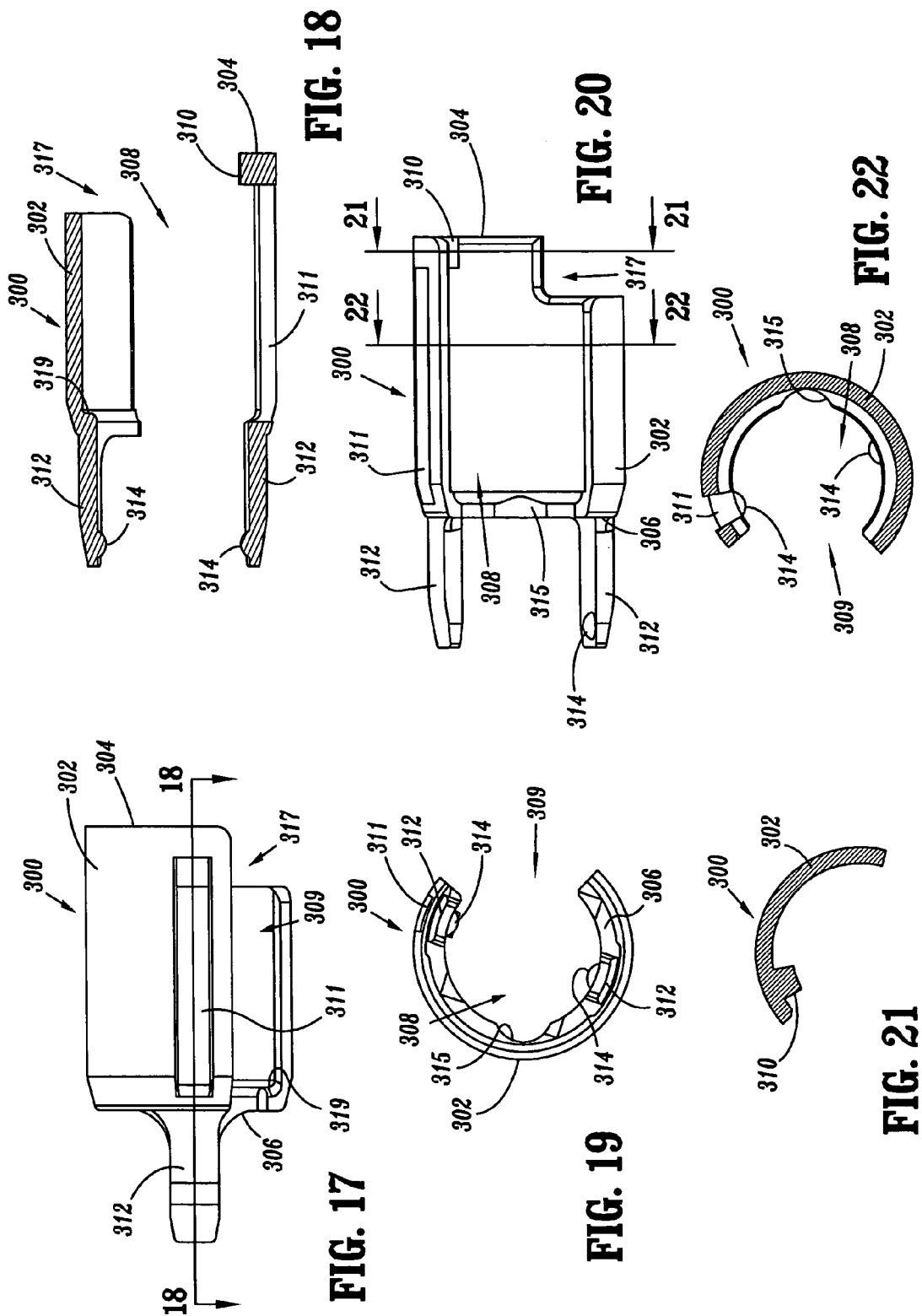

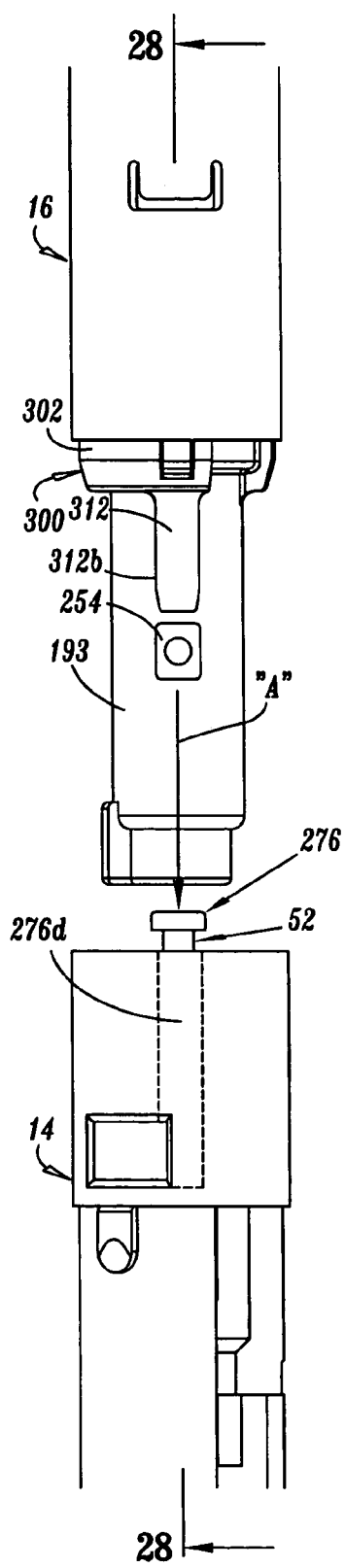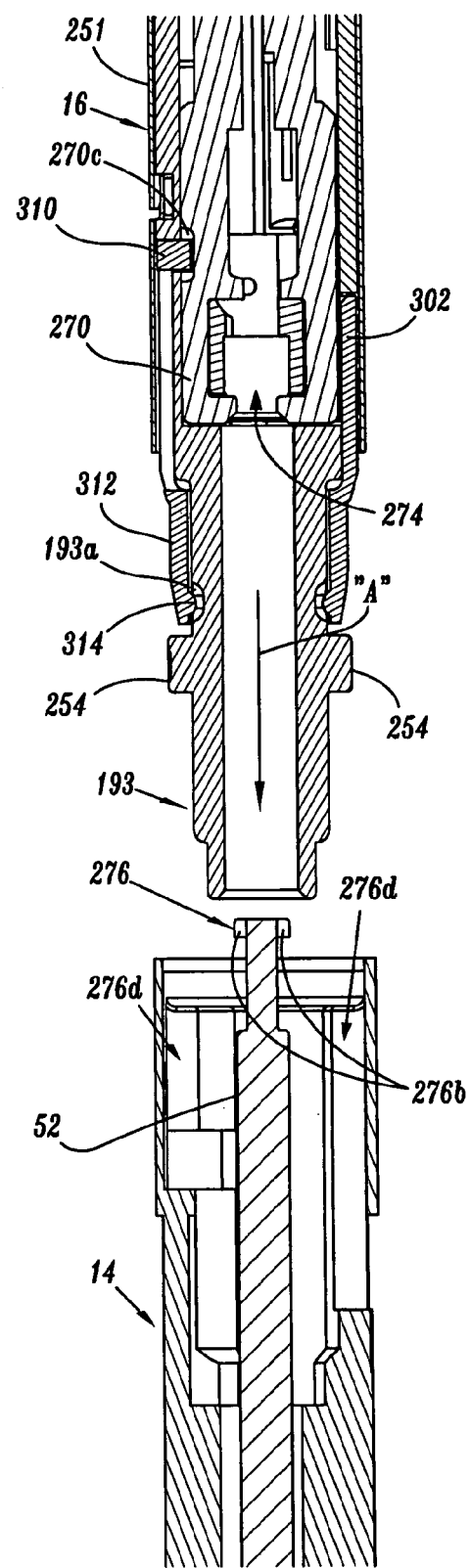
FIG. 27  FIG. 28

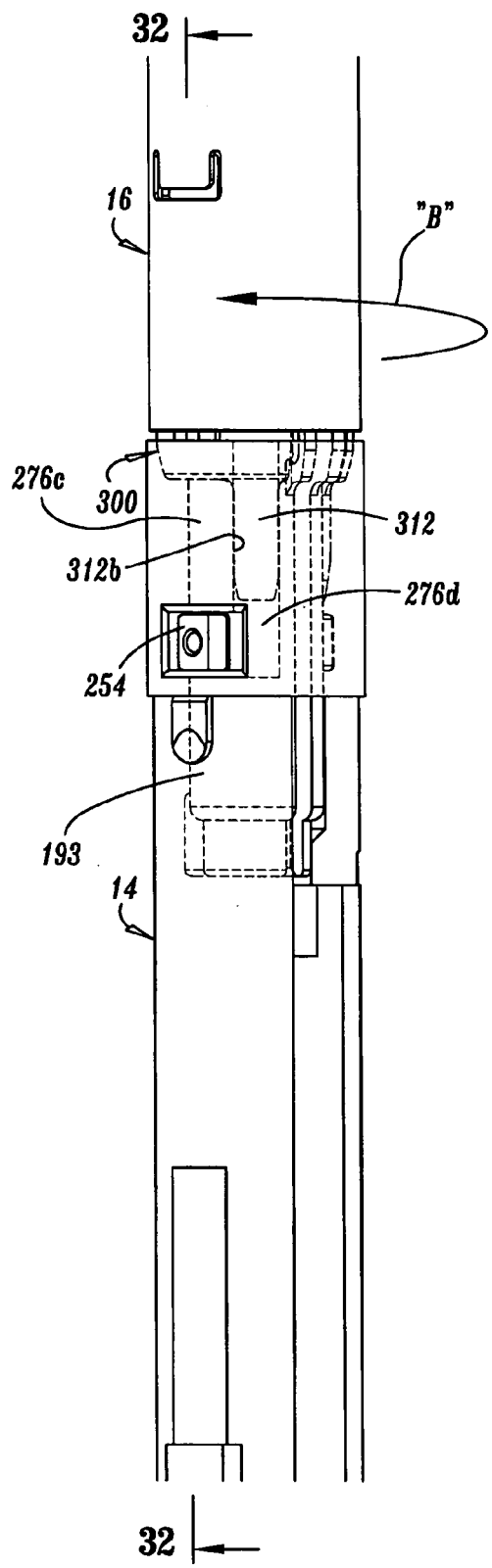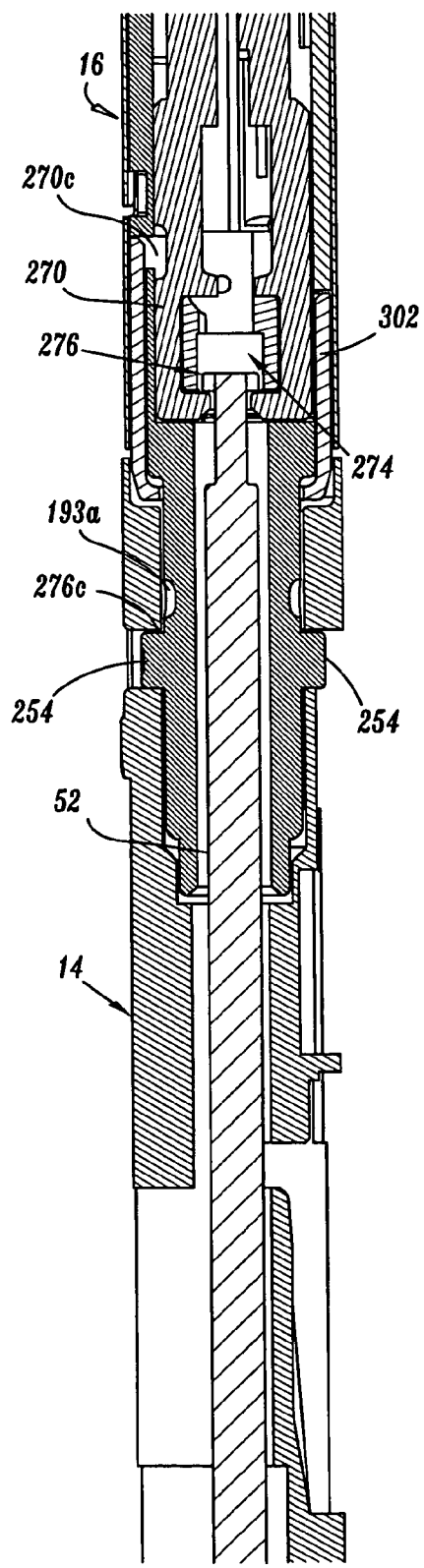
FIG. 31  FIG. 32

SURGICAL STAPLING APPARATUS WITH LOCKING MECHANISM

CROSS-REFERENCE TO RELATED APPLICATION

The present application claims the benefit of and priority to U.S. Provisional Application Ser. No. 60/545,619, filed Feb. 17, 2004, the entire content of which being incorporated herein by reference.

BACKGROUND

1. Technical Field

The present disclosure relates to a surgical apparatus, e.g., a surgical stapling apparatus. More particularly, the present disclosure relates to an endoscopic surgical stapling apparatus that includes a locking mechanism including a locking member for retaining the drive assembly of a loading unit, e.g., a single use loading unit ("SULU") or disposable loading unit ("DLU"), at a substantially fixed axial position until the SULU or DLU has been loaded with or secured to a surgical stapling apparatus, to ensure proper or complete engagement of the SULU or DLU, especially its drive assembly, to the surgical stapling apparatus. For simplicity, hereinafter, SULU or DLU will be referred to as "DLU", but it should be understood to include either or both a DLU or SULU.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated jaw members which are respectively used to capture or clamp tissue. Typically, one of the jaw members carries a staple cartridge which houses a plurality of staples arranged in at least two lateral rows while the other jaw member has an anvil that defines a surface for forming the staple legs as the staples are driven from the staple cartridge. Generally, the stapling operation is effected by cam members that travel longitudinally through the staple cartridge, with the cam members acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 also applies a double row of staples on each side of the incision. This patent discloses a surgical stapler that has a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above is designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); U.S. Pat. No. 5,332,142 (Robinson, et al.); and U.S. Pat. No. 6,241,139 (Milliman et al.), the entire contents of each of which are incorporated herein by reference.

Tyco Healthcare Group, LP, the assignee of the present application, has manufactured and marketed endoscopic stapling instruments, such as the Multifire ENDO GIA™ 30 and Multifire ENDO GIA™ 60 instruments, for a number of years. These instruments include a surgical stapling apparatus and a DLU. Typically, the DLU is attached to the apparatus immediately prior to surgery. After use, the DLU can be removed from the apparatus and a new DLU can be fastened to the apparatus to perform additional stapling and/or cutting operations. These instruments have provided significant clinical benefits. Nonetheless, improvements to these instruments are still possible.

It would be desirable to provide an improved DLU for a surgical stapling apparatus and an improved surgical stapling apparatus having the DLU loaded thereon.

It would also be desirable to provide a locking member for a DLU to assure proper loading of the DLU to the shaft of a surgical stapling apparatus.

Accordingly, it is an object of this disclosure to provide an improved DLU which locks or retains its drive assembly in proper position to be loaded onto the shaft of a surgical stapling apparatus (hereinafter referred to as the or a "ready-to-load position") until the DLU is loaded onto a surgical stapling apparatus to assure that when the DLU is loaded thereto, the drive assembly is properly engaged by, coupled to or connected to a drive member of the shaft, thereby helping to ensure proper operation of the DLU and the surgical stapling apparatus. For example, with the DLU loaded onto the surgical stapling apparatus, after firing of the surgical stapling apparatus, retraction of the control rod will unapproximate or open and/or unclamp the anvil and cartridge assemblies.

An object of the disclosure is to provide an improved DLU that includes a locking member that retains the drive assembly in such ready-to-load position until the DLU is loaded onto the surgical stapling apparatus.

Another object of the disclosure is to provide such a locking member for a DLU.

Another object of the present disclosure is to provide a locking member for a DLU and a DLU having a locking member, such that firing of the surgical stapling apparatus is prevented unless and until the DLU is loaded onto the shaft of the surgical stapling apparatus.

Yet another object of the disclosure is to provide a DLU that, after firing, can be disconnected from the surgical stapling apparatus.

Still another object of the disclosure is to provide a DLU that has only two conditions, one in which it is not loaded and its drive assembly is locked or retained in the ready-to-load position, and another in which the DLU is loaded onto the shaft of a surgical stapling apparatus and in which the drive assembly is unlocked and free to be actuated.

Still another object of the present disclosure is to provide the above objects in a roticulating, i.e., roticulable, DLU.

SUMMARY

In accordance with the present disclosure, a surgical apparatus, e.g., a surgical stapling apparatus, which includes structure for cooperating with a locking mechanism or member of a disposable loading unit for ensuring proper engagement of the disposable loading unit to an end of the surgical apparatus is provided. According to one aspect of the present disclosure, the surgical apparatus includes a housing, a handle supported by the housing, and a loading unit, e.g., a DLU, removably supportable on a distal end of the housing. Preferably, the DLU includes a housing portion including a distal end and a proximal end, a drive assembly slidably supported within the housing portion of the DLU and a locking mechanism or member supported on the housing portion of the DLU. The locking member has a first position wherein the locking member engages and maintains the drive assembly in a ready-to-load position relative to the housing portion, e.g. the proximal end of the housing portion of the DLU. The locking member also has a second position wherein the locking member permits movement of the drive assembly relative to the housing portion.

The drive assembly preferably includes a notch. The locking member preferably includes a cuff-like body portion that substantially surrounds a portion of the proximal end of the housing portion of the housing portion. The locking member further includes a tooth that extends radially inward from the body portion and that is engagable with a notch formed in the drive assembly. In the first position of the locking member, the tooth engages the notch of the drive assembly and maintains the drive assembly in the ready-to-load position. In the second position of the locking member, the tooth is disengaged from the notch of the drive assembly.

The proximal end of the housing portion of the DLU can include an annular slot formed therein, to receive the tooth of the locking member therein.

Preferably, the surgical apparatus is a surgical fastener, preferably a surgical stapler, and more preferably, a laparoscopic or endoscopic surgical stapler.

It is envisioned that the locking member has a proximal end that has at least one finger that extends axially therefrom. As such, when the locking member is in the first position, the finger is axially aligned with a nub extending radially outward from the proximal end of the housing portion and when the locking member is in the second position, the finger is not in axial alignment with the nub of the proximal end of the housing portion.

It is envisioned that the housing can have a projection that extends or is extendable radially inward thereof to move the locking member from the first position. In particular, the projection is configured to act on a side surface of the finger of the locking ring as the DLU is rotated into engagement with the housing.

The surgical apparatus may include an elongate body extending from the housing.

Desirably, the housing portion of the DLU defines an insertion tip.

The present disclosure also provides for a loading unit for use with a surgical stapling apparatus. The loading unit includes a housing portion having a distal end and a proximal end, a drive assembly slidably supported within the housing portion of the loading unit, and a locking member supported on the housing portion of the loading unit. The locking member is movable from a first position wherein the locking member engages the drive assembly and maintains the drive assembly in a ready-to-load position to a second position wherein the locking member permits movement of the drive assembly relative to the housing portion.

The present disclosure further provides for a locking member for maintaining a drive assembly of a loading unit in a ready-to-load position when the loading unit is coupled to a surgical stapling apparatus. The locking member includes a cuff-like body portion that at least partially surrounds a proximal end of the loading unit, and a tooth extending radially inward from the body portion, wherein the tooth selectively engages a notch formed in the drive assembly such that when the locking member is in a first position the tooth engages the notch of the drive assembly and maintains the drive assembly in the ready-to-load position, and when the locking member is in a second position the tooth is disengaged from the notch of the drive assembly.

Additional advantages will become apparent from the description which follows, taken in conjunction with the accompanying drawings.

BRIEF DESCRIPTION OF THE DRAWINGS

The present disclosure will be further described with reference to the accompanying drawings, wherein like reference numerals refer to like parts in the several views, and wherein:

FIG. 7 is a top perspective view of the DLU of FIG. 6;

FIG. 8 is a top perspective view of the DLU of FIGS. 6 and 7;

FIG. 12 is a top perspective view of the axial drive assembly of FIG. 11 of the DLU of FIGS. 6–9;

FIG. 13 is an enlarged top perspective view of the lower housing half of the proximal housing portion of the DLU of FIGS. 6–9;

FIG. 17 is a top elevational view of the locking member of FIGS. 15 and 16;

FIG. 18 is a longitudinal cross-sectional view of the locking member of FIGS. 15–17, as taken through 18—18 of FIG. 17;

FIG. 19 is a front elevational view of the locking member of FIGS. 15–18;

FIG. 20 is a side elevational view of the locking member of FIGS. 15–19;

FIG. 21 is a transverse cross-sectional view of the locking member of FIGS. 15–20, as taken through 21—21 of FIG. 20;

FIG. 22 is a transverse cross-sectional view of the locking member of FIGS. 15–20, as taken through 22—22 of FIG. 20;

FIG. 27 is a top plan view, with portions broken away, illustrating a first stage in the attachment of the DLU of FIGS. 6–9 to the elongate body of the surgical stapling apparatus shown in FIGS. 1–3;

FIG. 28 is a longitudinal cross-sectional view of the first stage in the attachment of the DLU of FIGS. 6–9 to the elongate body of the surgical stapling apparatus shown in FIGS. 1–3, as taken along line 28—28 of FIG. 27;

FIG. 31 is a top plan view, with portions broken away, illustrating a third stage in the attachment of the DLU of FIGS. 6–9 to the elongate body of the surgical stapling apparatus shown in FIGS. 1–3; and FIG. 32 is a longitudinal cross-sectional view of the third stage in the attachment of the DLU of FIGS. 6–9 to the elongate body of the surgical stapling apparatus shown in FIGS. 1–3, as taken along line 32—32 of FIG. 31.

DETAILED DESCRIPTION OF PREFERRED EMBODIMENTS

Figure 1:
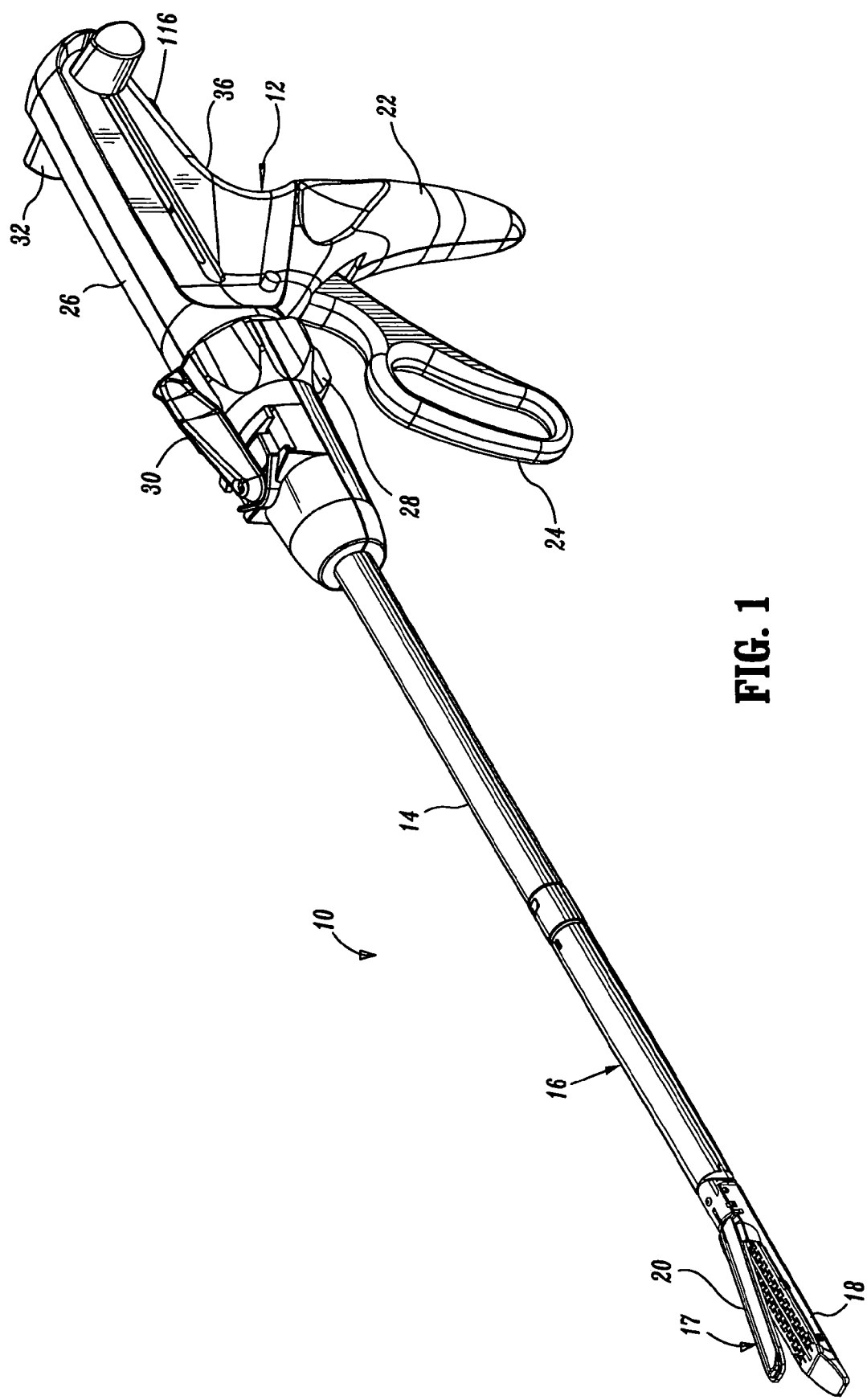
FIG. 1 is a top perspective view of a preferred embodiment of the presently disclosed surgical stapling apparatus.
Figure 2:
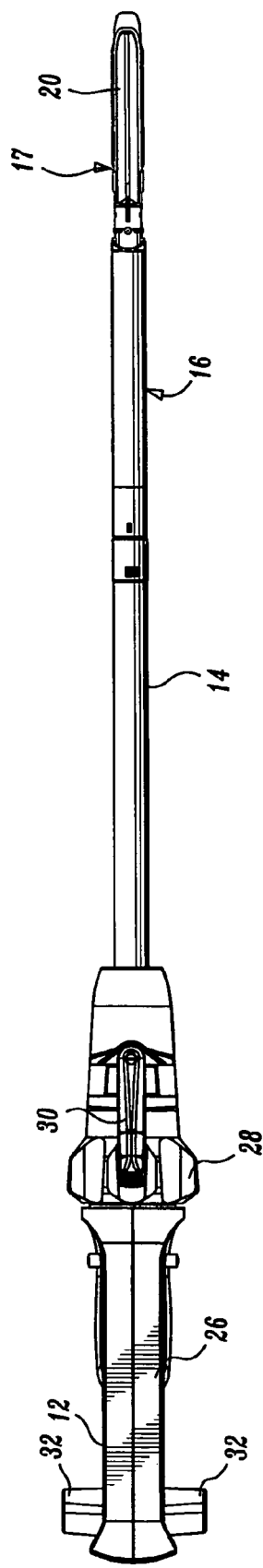
FIG. 2 is a top view of the surgical stapling apparatus shown in FIG. 1.
Figure 3:
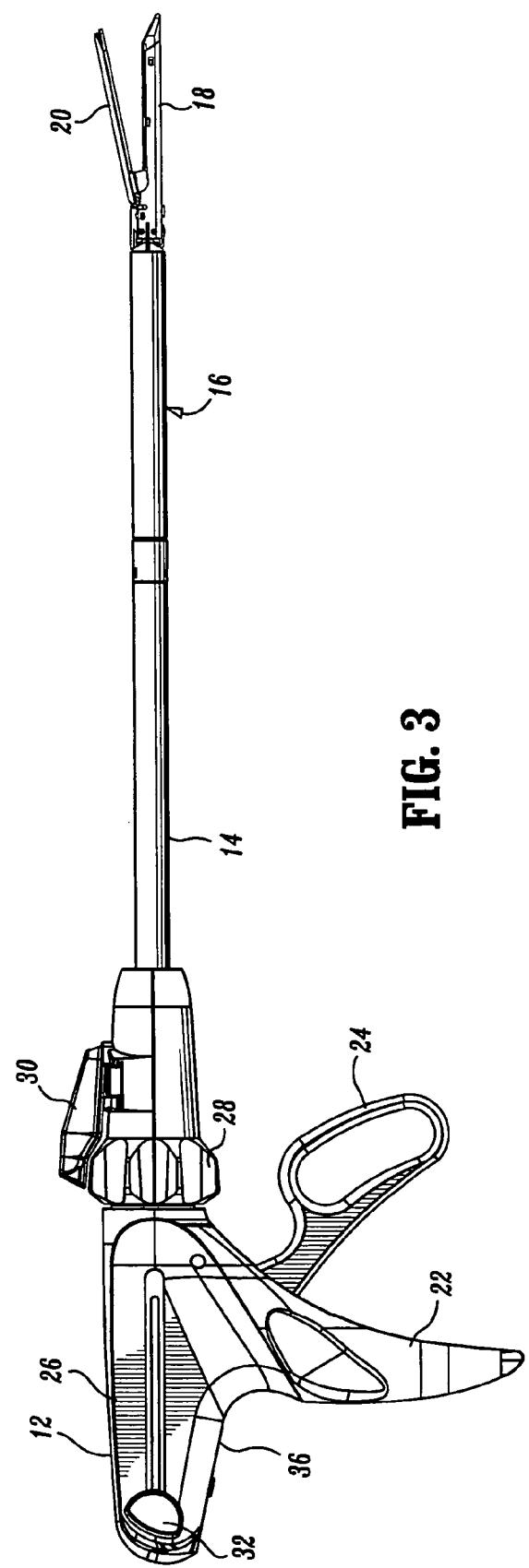
FIG. 3 is a side view of the surgical stapling apparatus shown in FIGS. 1 and 2.

Preferred embodiments of the presently disclosed surgical apparatus, DLU and locking mechanism or member will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term "distal" will refer to the end of the apparatus which is furthest from the operator.

FIGS. 1–4 show a surgical apparatus, e.g., surgical stapling apparatus, generally referred to as 10. In the interest of brevity, this disclosure will focus primarily on systems, methods and structures for loading, engaging, coupling or connecting a disposable loading unit ("DLU") 16 to surgical stapling apparatus 10. A detailed discussion of the remaining components and method of use of surgical stapling apparatus 10, is disclosed in U.S. Pat. No. 6,241,139.

Surgical stapling apparatus 10 is an endoscopic apparatus and includes a handle assembly 12 and an elongated body 14 extending from handle assembly 12. A DLU 16 is releasably secured to the distal end of elongated body 14. While this disclosure relates to the use of a DLU with surgical stapling apparatus 10, it is understood and within the scope of the present disclosure that a single use loading unit (SULU) or other end effector and/or tool assembly can equally be used in cooperation with surgical stapling apparatus 10.

DLU 16 includes a tool 17 having a cartridge assembly 18 housing a plurality of surgical staples (not shown) and an anvil assembly 20 movably secured in relation to cartridge assembly 18. As shown herein, DLU 16 is configured to apply six (6) linear rows of staples, in DLU's measuring from about 30 mm to about 60 mm in length. DLUs for applying any number of rows of staples, having staple pockets arranged in various patterns and/or DLUs and end effectors having any other lengths, e.g., 45 mm, are also envisioned. Handle assembly 12 includes a stationary handle member 22, a movable handle member 24, and a barrel portion 26.

A rotatable member 28 preferably is mounted on the forward end of barrel portion 26 to facilitate rotation of elongated body 14 and attached DLU 16 with respect to handle assembly 12. An articulation lever 30 preferably is also mounted on the forward end of barrel portion 26 adjacent rotatable member 28 to facilitate articulation of tool assembly 17. Preferably, a pair of knobs 32 are movably positioned along barrel portion 26. Knobs 32 are advanced distally to approximate or close cartridge and/or anvil assembly 18, 20, and retracted proximally to unapproximate or open cartridge and/or anvil assembly 18, 20.

Figure 4:
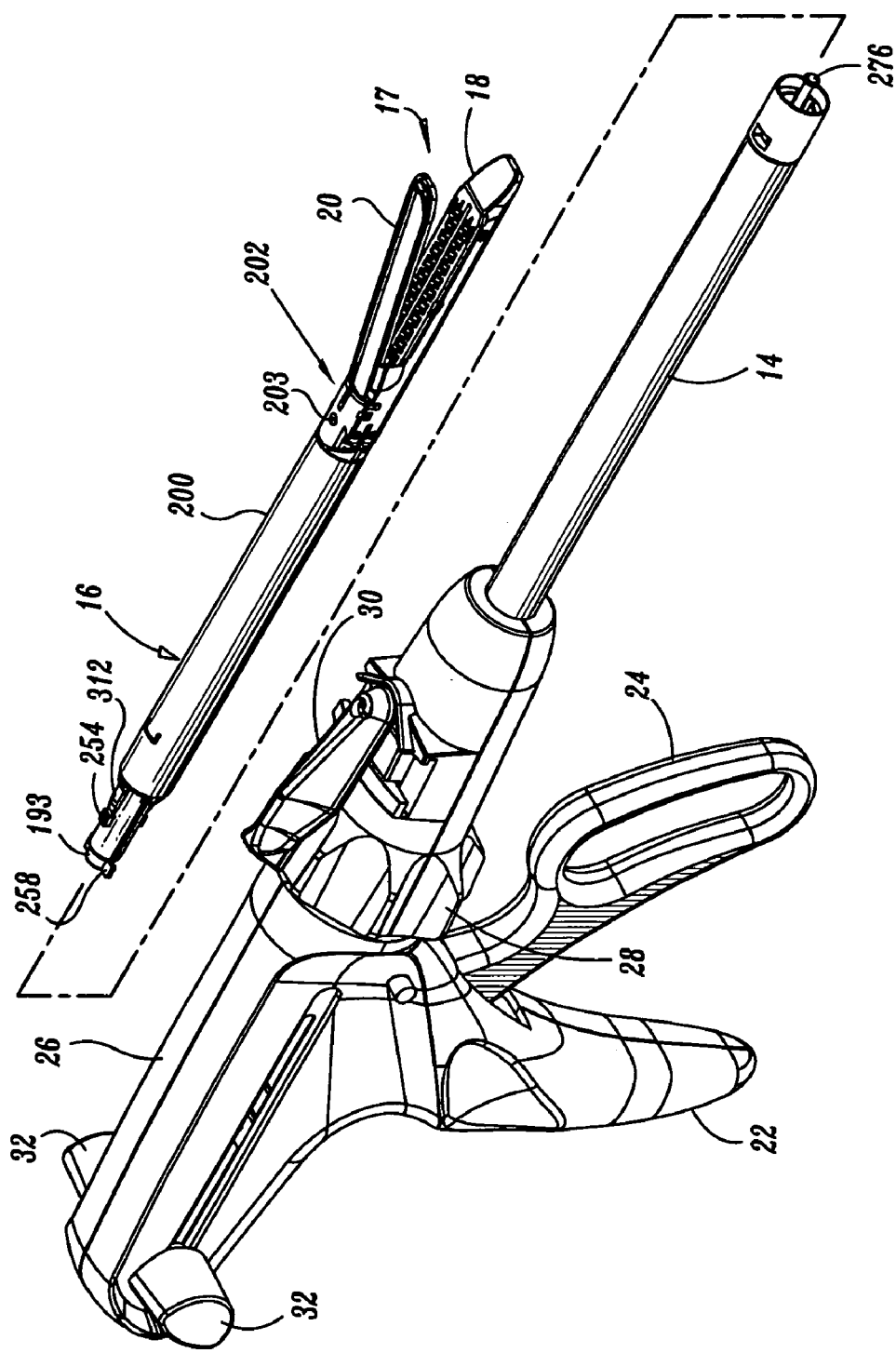
FIG. 4 is a top perspective view of the surgical stapling apparatus of FIGS. 1–3 with the DLU disengaged from the elongate body of the surgical stapling apparatus.

As seen in FIG. 4, DLU 16 is desirably selectively removably couplable to elongated body 14. DLU 16 includes a housing portion 200 having a proximal end adapted to releasably engage the distal end of elongated body 14. A mounting assembly 202 is pivotally secured at 203 to the distal end of housing portion 200, and is configured to receive the proximal end of tool assembly 17 such that pivotal movement of mounting assembly 202 about an axis at 203 perpendicular to the longitudinal axis of housing portion 200 effects articulation of tool assembly 17.

Figure 5:
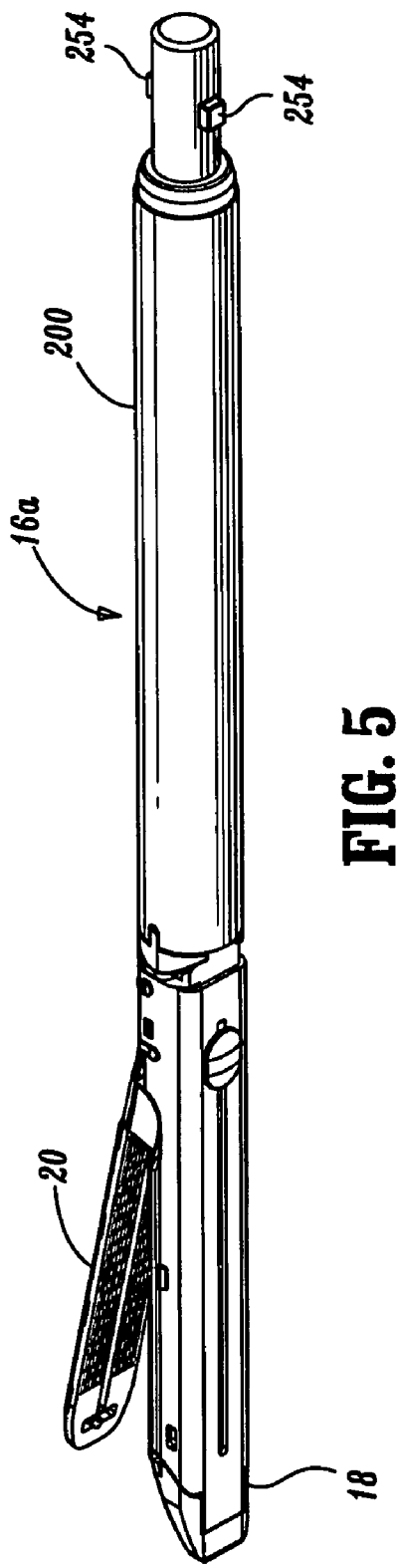
FIG. 5 is a bottom perspective view of a non-articulating DLU for use with the surgical stapling apparatus of FIGS. 1–4.
Figure 6:
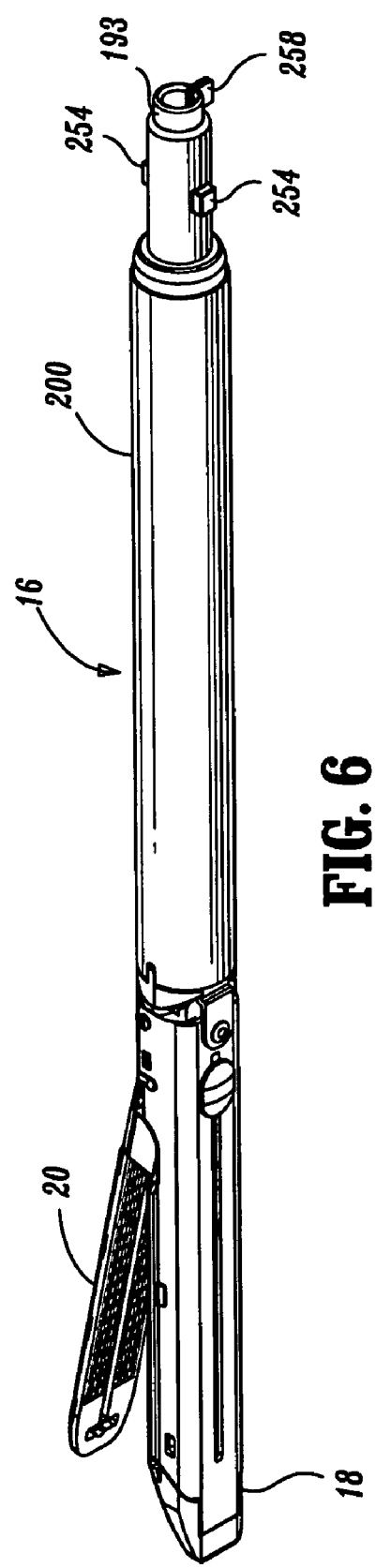
FIG. 6 is a bottom perspective view of the preferred articulating DLU of the surgical stapling apparatus of FIGS. 1–4.

FIGS. 5–8 show various perspective views of DLU 16. Surgical stapling apparatus 10 is capable of receiving a non-articulating DLU 16a, as seen in FIG. 5, or an articulating DLU 16, as seen in FIGS. 6–8. U.S. Pat. No. 6,241,139 includes a detailed discussion of articulating and non-articulating DLU.

Figure 9:
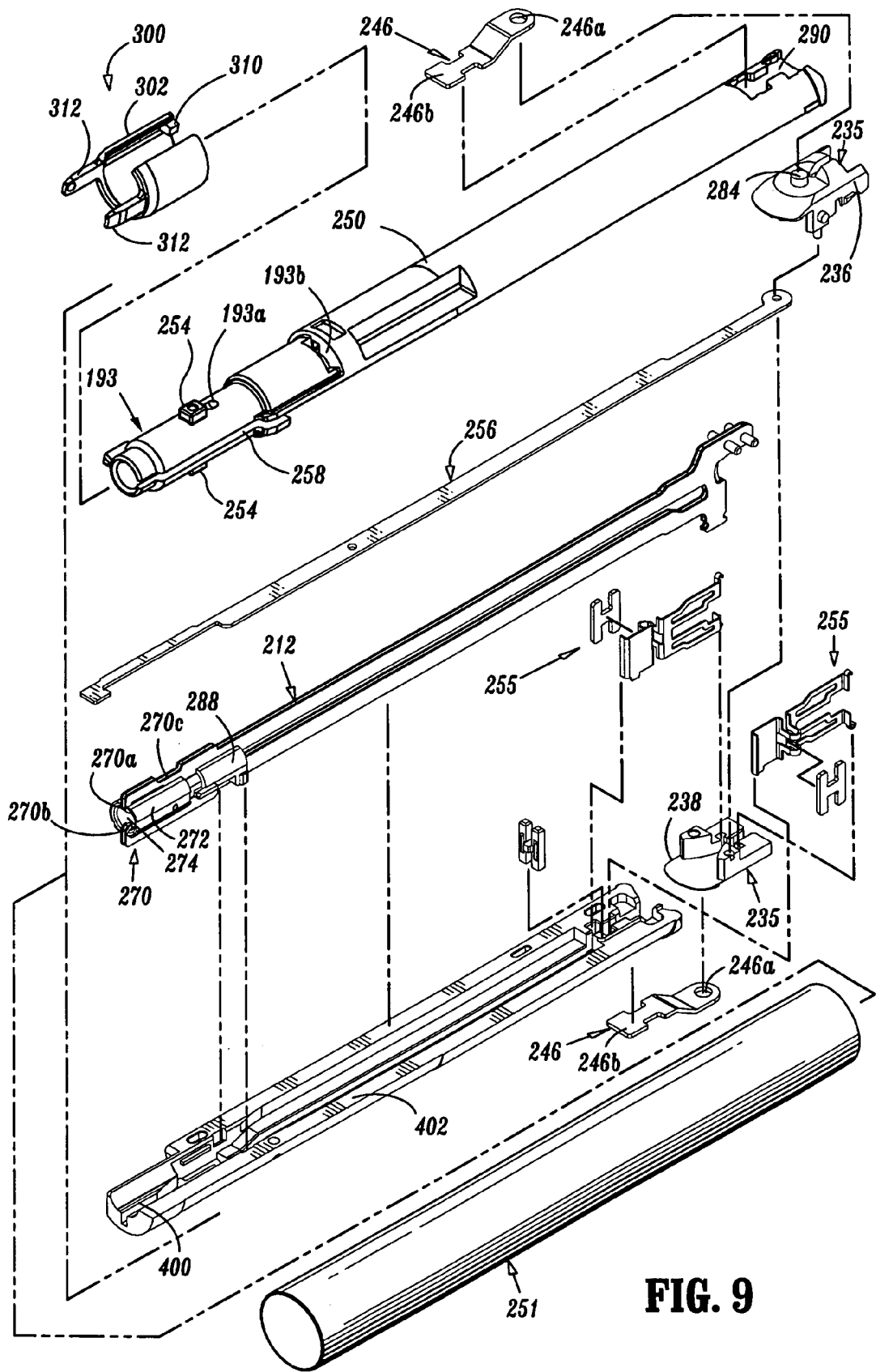
FIG. 9 is an enlarged top perspective view, with parts separated, of the proximal housing portion and mounting assembly of the DLU of FIGS. 6–8.
Figure 10:
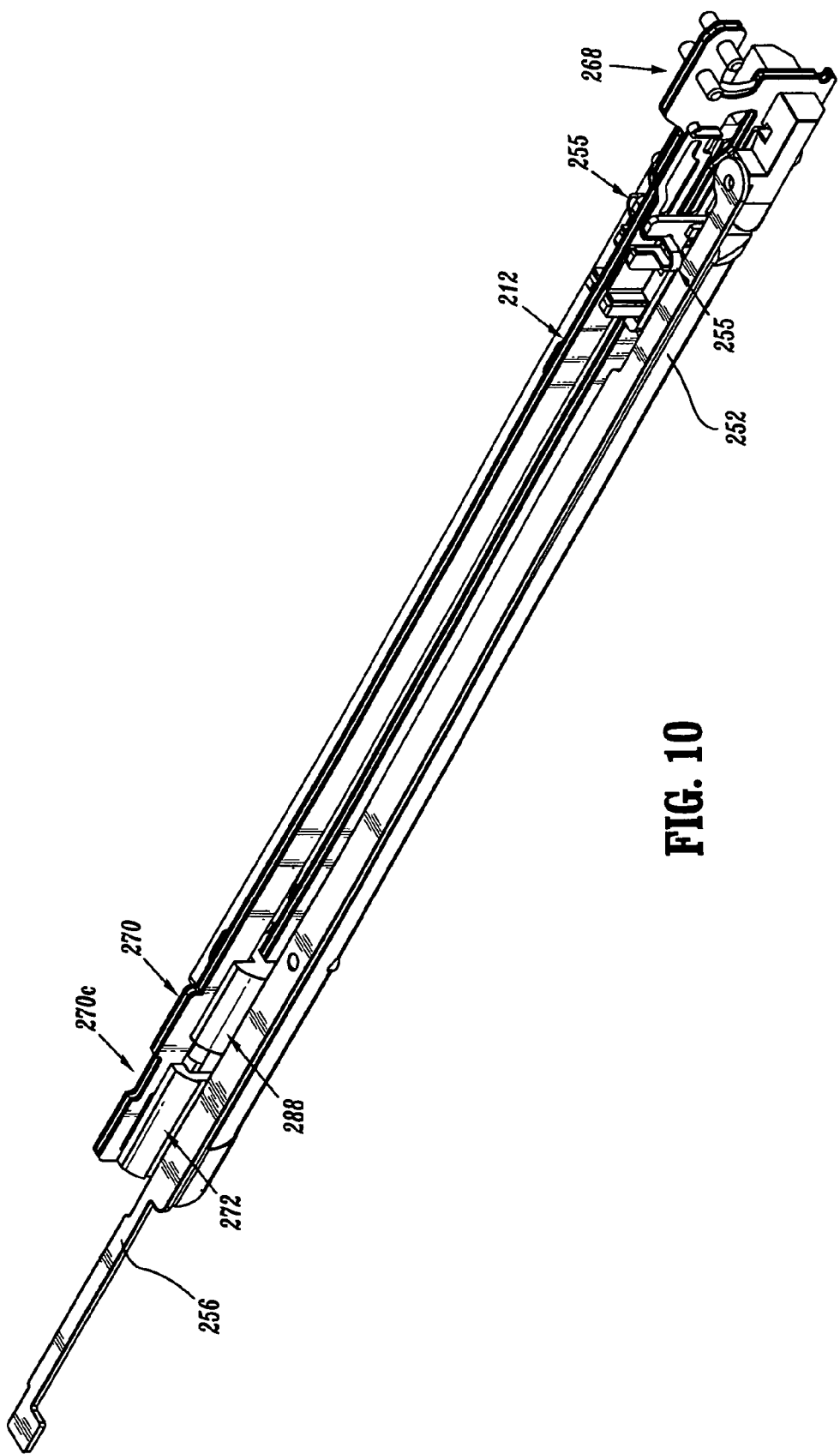
FIG. 10 is a top perspective view of the proximal housing portion and mounting assembly of the DLU of FIGS. 6–9 with the upper housing half removed.

With general reference to FIGS. 9, 10, 13 and 23–26 and particular reference to FIGS. 9, 10 and 13, DLU 16 includes a mounting assembly 235. Mounting assembly 235 includes an upper and a lower mounting portion 236, 238, respectively. A centrally located pivot member 284 extends from each of upper and lower mounting portions 236, 238 through respective openings 246a formed in coupling members 246. Coupling members 246 each include an interlocking proximal portion 246b configured to be received in grooves 290 formed in the proximal end of upper and lower housing halves 250, 252 to retain mounting assembly 235 and upper and lower housing halves 250, 252 in a longitudinally fixed position in relation to each other.

Upper housing half 250 and lower housing half 252 are contained within an outer sleeve, shell or casing 251. The proximal end of upper housing half 250 includes engagement nubs 254 for releasably engaging the distal end of body 14. Nubs 254 form a bayonet-type coupling with the distal end of body 14. Housing halves 252 and 254 define a channel 400 for slidably receiving axial drive assembly 212 therein. An articulation link 256 is dimensioned to be slidably positioned within a slot 402 formed in upper and lower housing halves 250, 252. A pair of blow out plate assemblies 255 are positioned adjacent the distal end of housing portion 200 adjacent the distal end of axial drive assembly 212 to prevent outward buckling and bulging of drive assembly 212 during articulation and firing of surgical stapling apparatus 10. For a detailed discussion of the structure and operation of blow out plate assemblies 255, reference is made to International Application Serial No. PCT/US02/32031, filed on Oct. 4, 2002, entitled "Surgical Stapling Device", the entire content of which is herein incorporated by reference.

Referring to FIG. 9, optionally, a locking member 288 may be supported on engagement section 270 of axial drive assembly 212. In operation, when axial drive assembly 212 is actuated, by applying a predetermined force to movable handle member 24 to advance axial drive assembly 212 distally, locking member 288 provides an audible and tactile indication that surgical stapling apparatus 10 has been actuated. For a detailed discussion of the structure and operation of locking member 288, reference is made to the aforementioned International Application Serial No. PCT/US02/32031. Locking member 288 may also prevent inadvertent partial actuation of DLU 16, such as during shipping, by locking axial drive assembly 212 at a fixed position within DLU 16 until a predetermined axial force has been applied to axial drive assembly 212.

Figure 11:
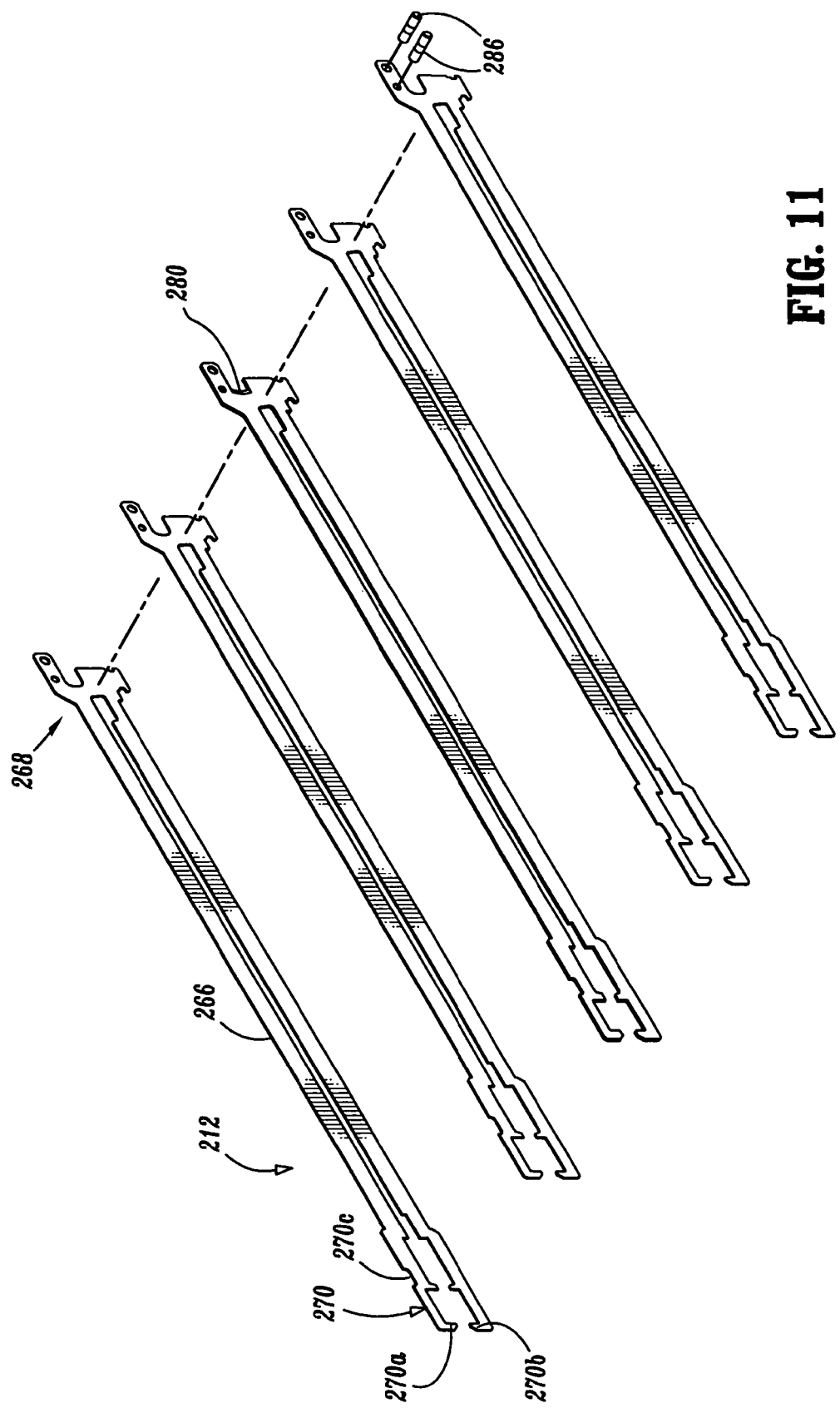
FIG. 11 is a top perspective view, with parts separated, of the axial drive assembly of the DLU of FIGS. 6–9.

With reference to FIGS. 9–12, axial drive assembly 212 includes an elongated drive beam 266 (FIG. 11) including a distal working head 268 (FIG. 12) and a proximal engagement section 270. Drive beam 266 may be constructed from a single sheet of material or, preferably, multiple stacked sheets, as shown in FIG. 11. Engagement section 270 includes a pair of resilient engagement fingers 270a and 270b which are dimensioned and configured to mountingly engage a pair of corresponding retention slots 272a and 272b formed in drive member 272 (FIG. 12). Drive member 272 includes a proximal porthole 274 configured to receive distal end 276 of a drive member, e.g., drive rod or control rod 52 (FIGS. 14 and 16–18) when the proximal end of DLU 16 is being engaged with elongated body 14 of surgical stapling apparatus 10. Control rod 52 functions to impart axial movement of drive assembly 212 from handle assembly 12.

With reference to FIGS. 9 and 15–32, DLU 16 further includes a locking member 300 rotatably supported on insertion tip 193 and/or on upper and lower housing halves 250, 252. Locking member 300 is preferably movable or manipulatable from a first position (FIGS. 23 and 24), in which locking member 300 maintains drive assembly 212 in a ready-to-load position, to a second position (FIGS. 25 and 26), in which drive assembly 212 is free to move axially. DLU 16 is considered to be loaded to elongate body 14 when locking member 300 is in the second position, i.e., when drive assembly 212 is connected to control rod 52 of elongate body 14.

Figure 24:
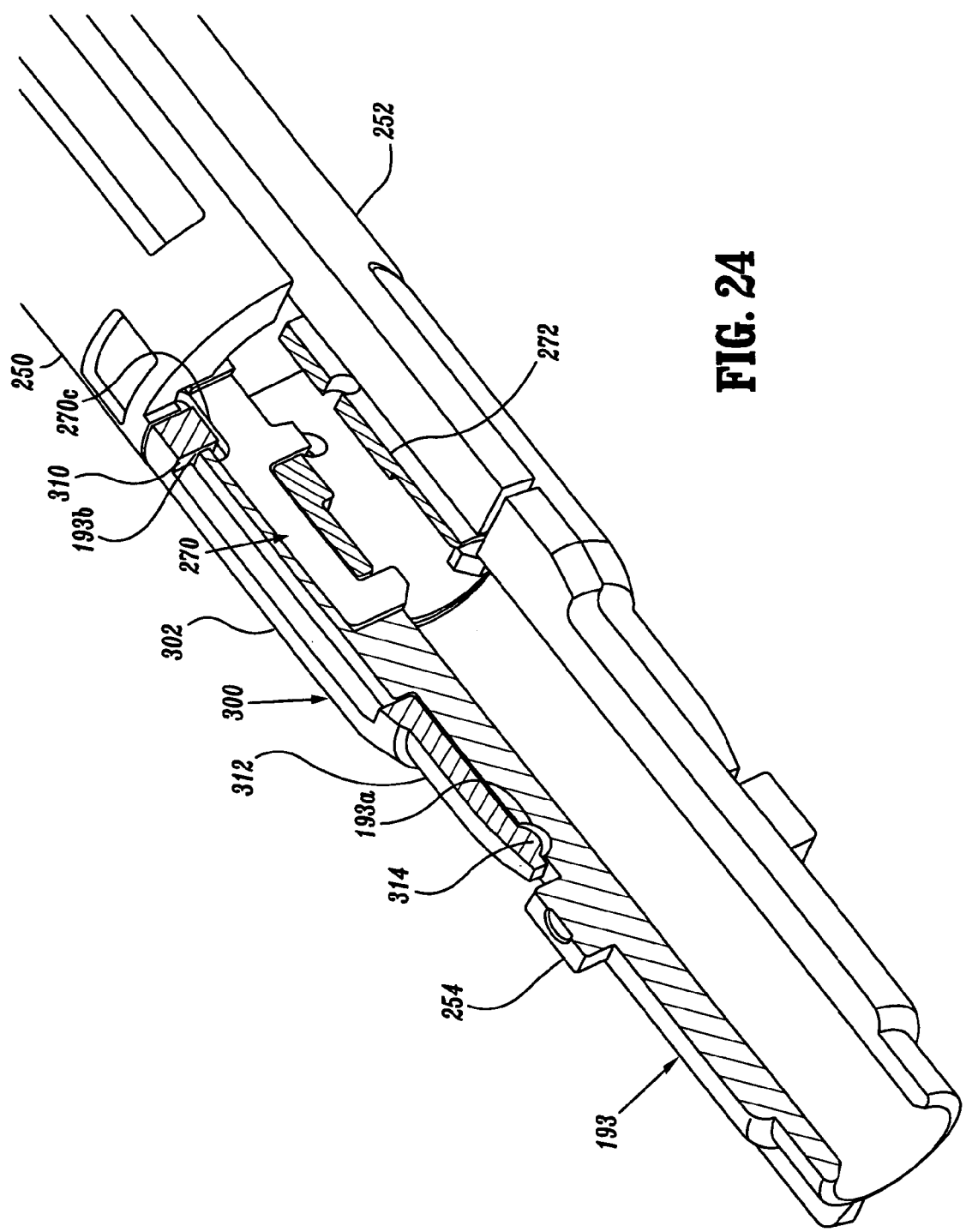
FIG. 24 is an enlarged perspective view, partially cut away, of the proximal end of the DLU of FIGS. 6–9 further illustrating the locking member situated in the first position.

As additionally seen in FIGS. 15–22, locking member 300 includes a substantially cylindrical, preferably sleeve or cuff-like, body portion 302 including a distal end 304, a proximal end 306 and defining a passage 308 therethrough. Locking member 300 further includes a projection or tooth 310 extending radially inward from body portion 302 near distal end 304. In use, as best seen in FIG. 24 and as will be discussed in greater detail below, when locking member 300 is in a first position (i.e., in a "ready-to-load", locked or coupled position), tooth 310 engages a notch or recess 270c (FIG. 9) formed in the edge of engagement section 270 of drive assembly 212 to thereby effectively axially lock and maintain drive assembly 212 in the ready-to-load position (e.g., wherein drive assembly 212 is in a retracted or proximal-most position relative to upper housing half 250). Preferably, the locking mechanism of the present invention includes notch or recess 270c.

Accordingly, when DLU 16 is being coupled to the distal end of elongate body 14, locking member 300 ensures that engagement section 270 of drive assembly 212 is in a position to, and properly engages, couples with or connects to distal end 276 (FIG. 14) of control rod 52. Distal end 276 of control rod 52 has one or more engagement surfaces, preferably, and here shown as, including a head 276a and a smaller diameter annular recess 276b just proximal of head 276a and partially defined by head 276a. Thereafter, less preferably concomitantly therewith, locking member 300 is manipulated (here rotated) to a second position wherein drive assembly 212 is in an unlocked, operative position in which tooth 310 is released and/or otherwise disengaged from notch 270c of engagement section 270 of drive assembly 212 such that drive assembly 212 is free to move relative to housing portion 200 or upper and lower housing portions 250, 252 of DLU 16. As previously stated, when locking member 300 is in the second position, DLU 16 is considered loaded onto elongate body 14 of surgical stapling apparatus 10. Thus, drive assembly 212 is free to be actuated and reciprocated axially by drive rod 52 to perform its operative functions of approximating and closing anvil and cartridge assemblies 18, 20, driving knife 280 and firing staples, as well as of un-approximating, un-clamping, and retracting drive assembly 212.

Figure 25:
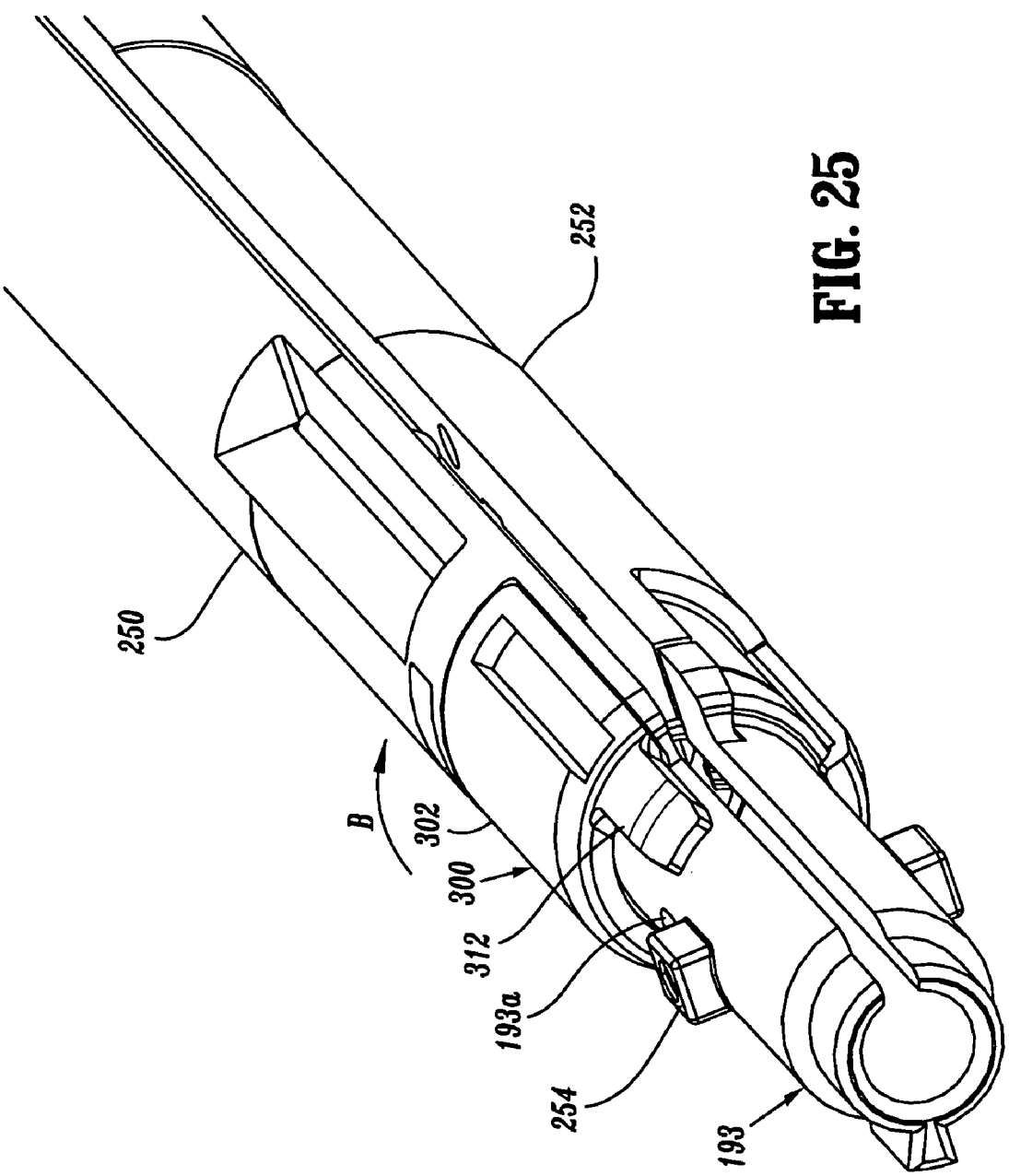
FIG. 25 is an enlarged perspective view of the proximal end of the DLU of FIGS. 6–9 illustrating the locking member situated in the second position.
Figure 26:
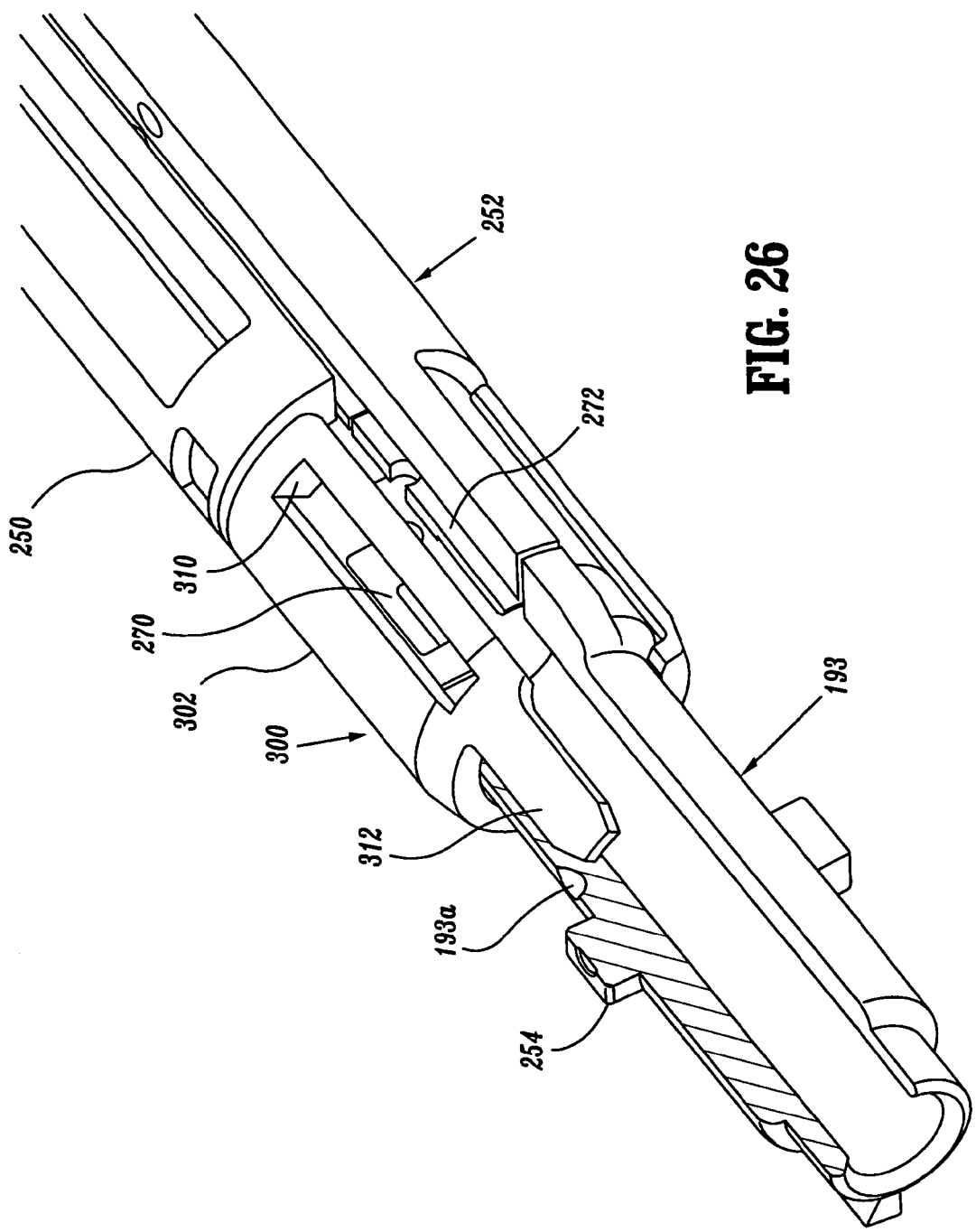
FIG. 26 is an enlarged perspective view, partially cut away, of the proximal end of the DLU of FIGS. 6–9 further illustrating the locking member situated in the second position.
Figure 29:
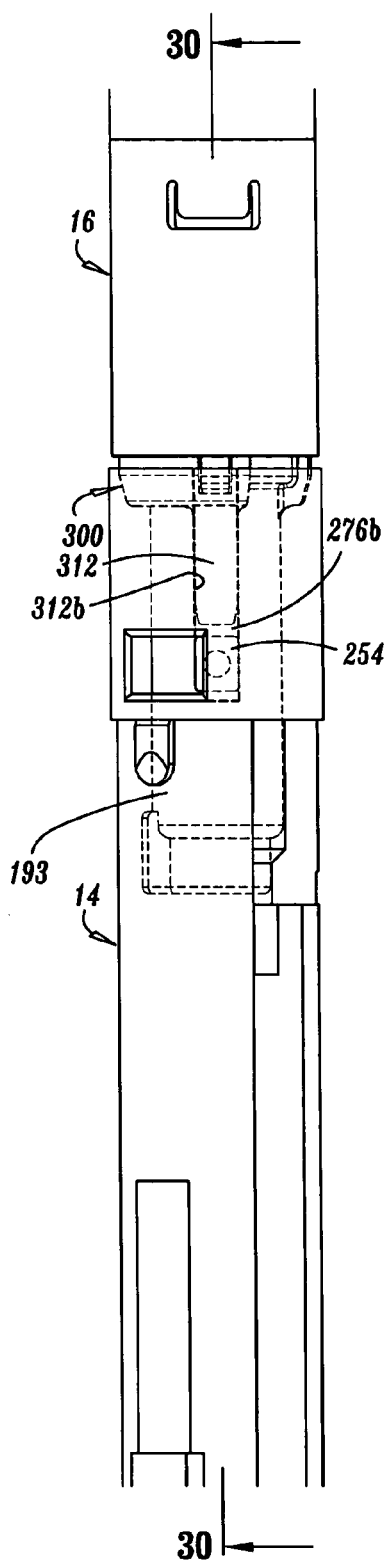
FIG. 29 is a top plan view, with portions broken away, illustrating a second stage in the attachment of the DLU of FIGS. 6–9 to the elongate body of the surgical stapling apparatus shown in FIGS. 1–3.
Figure 30:
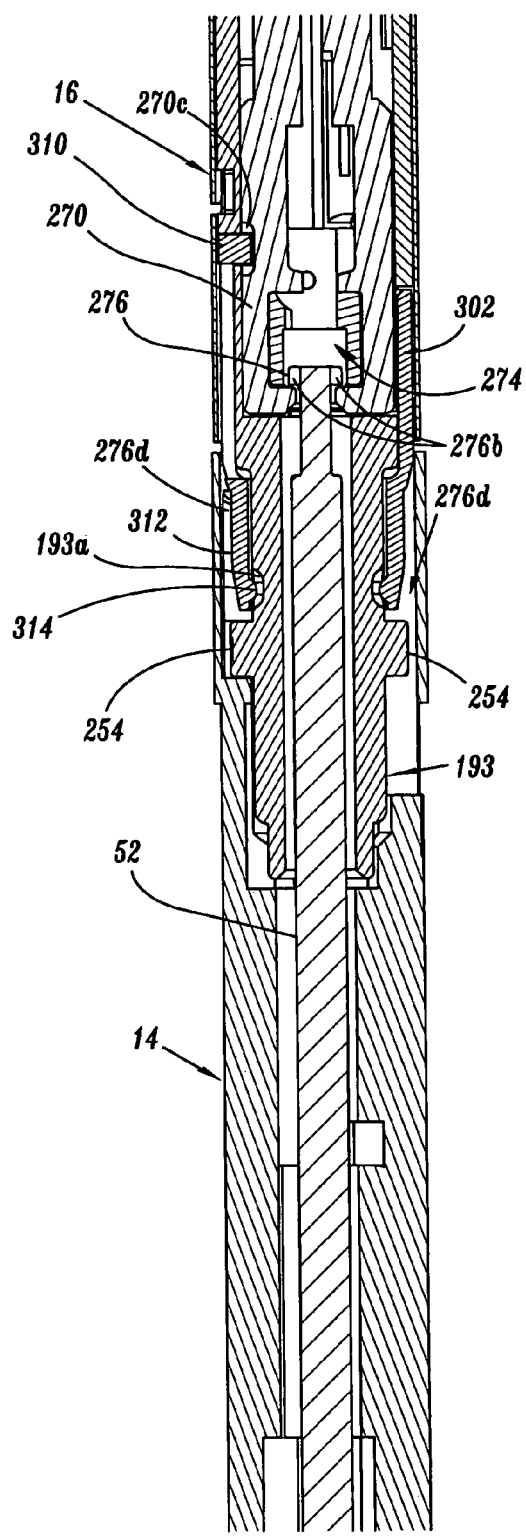
FIG. 30 is a longitudinal cross-sectional view of the second stage in the attachment of the DLU of FIGS. 6–9 to the elongate body of the surgical stapling apparatus shown in FIGS. 1–3, as taken along line 30—30 of FIG. 29.

With continued reference to FIGS. 15–22, locking member 300 further includes at least one finger 312 that extends longitudinally from proximal end 306. Preferably, locking member 300 includes a pair of fingers 312, at least one of which preferably each of which is axially aligned with tooth 310. At least one of, preferably both, fingers 312 include a protrusion, nub or detent 314 extending radially inward from an inner surface 312a of finger(s) 312. In use, as best seen in FIGS. 24–26 and as will be discussed in greater detail below, protrusion(s) 314 is/are selectively engagable with one or more recesses or dimples 193a formed in the outer surface of insertion tip 193. Preferably, when locking member 300 is in the first position, fingers 312 and dimples 193a are in axial alignment with nubs 254 extending radially outward from insertion tip 193. Protrusions 314 and dimples 193a are optionally part of the locking mechanism and create a snap-fit type friction engagement wherein protrusion 314 and dimples 193a cooperate with one another to prevent and/or otherwise inhibit locking member 300 from inadvertently or prematurely rotating from the first position where tooth 310 engages and axially locks drive assembly into position, to the second position in which tooth 310 is disengaged from drive assembly 212.

In addition, insertion tip 193 includes a cutout or annular slot 193b (FIG. 9) formed at least partially about the circumference of tip 193 to enable tooth 310 to pass therethrough and to lockingly engage with notch 270c of engagement section 270. Preferably, slot 193b has sufficient length and depth to allow for tooth 310 to extend below the inside surface of insertion tip 193 and to move within slot 193b as locking member 300 is moved, i.e., rotated, from its first position to its second position to disengage tooth 310 from notch 270c of engagement section 270.

As seen in FIG. 19, body portion 302 of locking member 300 extends annularly about 270° and thereby defines an opening 309 of about 90°. Opening 309 is preferably disposed between fingers 312. Preferably, one of fingers 312 is positioned at an angle of about 70° relative to the center line of opening 309 (FIGS. 19, 20 and 22). Preferably, fingers 312 are diametrically opposed to each other. Proximal end 306 of body portion 302 includes a stress reliever 315 formed therein. Preferably, stress reliever 315 is positioned at a location opposite opening 309. Stress reliever 315 enables body portion 302 to open up or radially expand in order for lock member 300 to be snapped onto or otherwise operatively coupled to insertion tip 193. Distal end 304 of body portion 302 defines a clearance notch 317 extending from opening 309 and substantially opposite tooth 310.

Locking member 300 further includes an aperture and/or window 311 formed in body portion 302 thereof. Aperture 311 is axially aligned with tooth 310 and finger 312. Aperture 311 is provided to facilitate the molding and/or fabrication of locking member 300 to facilitate the removal of locking member 300 from a corresponding fabrication mold and/or tool. Locking member 300 further includes a locating surface, here shoulder 319, formed along the inner circumference of body portion 302 at a position distal of proximal end 306.

Figures 14, 14A:
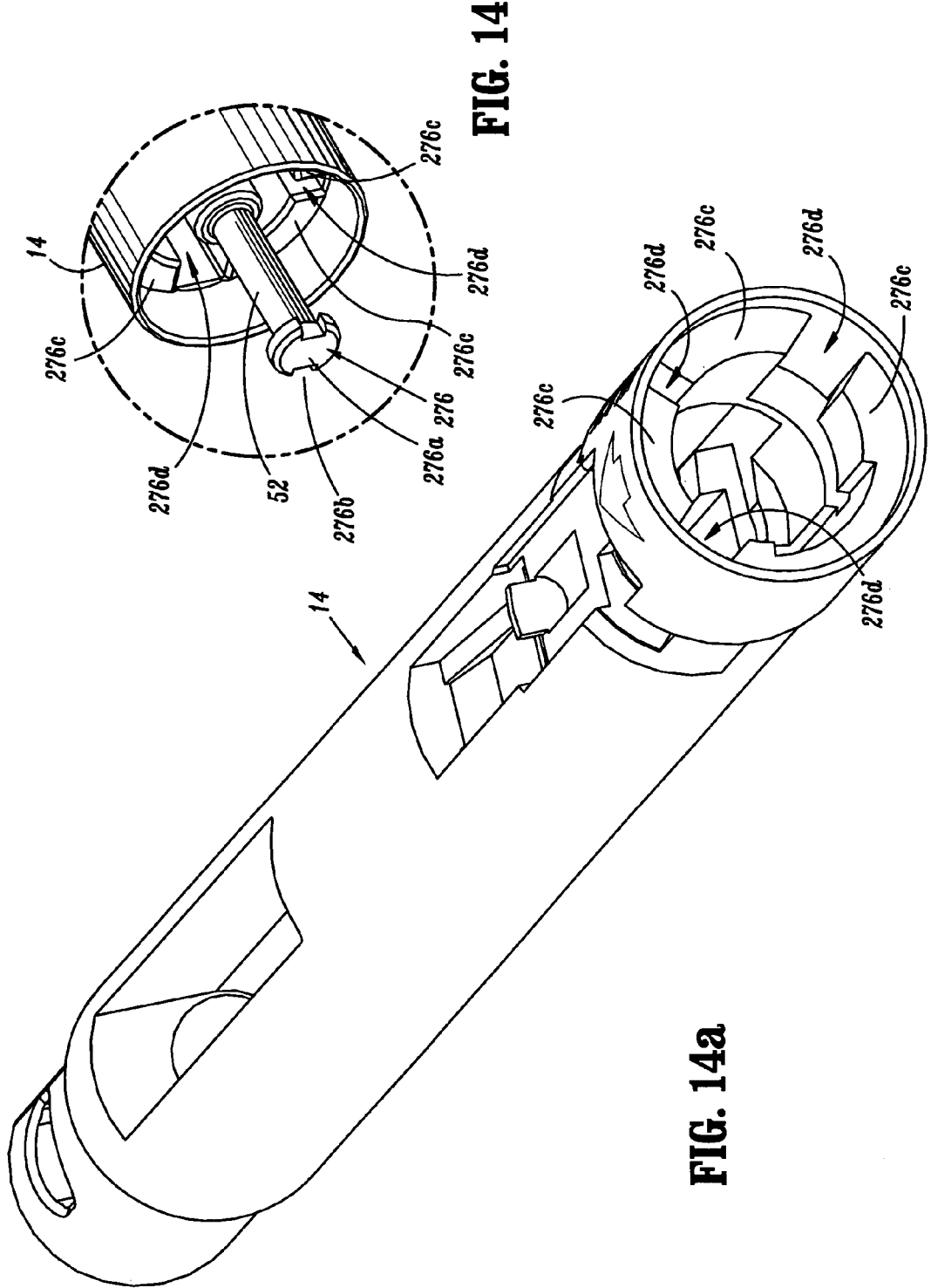
FIG. 14 is an enlarged perspective view of the distal end of the elongate body of the stapling apparatus shown in FIG. 4.
FIG. 14a is a further enlarged perspective view of the distal end of the elongate body of FIG. 14, shown without the control rod extending therethrough.
Figure 15:
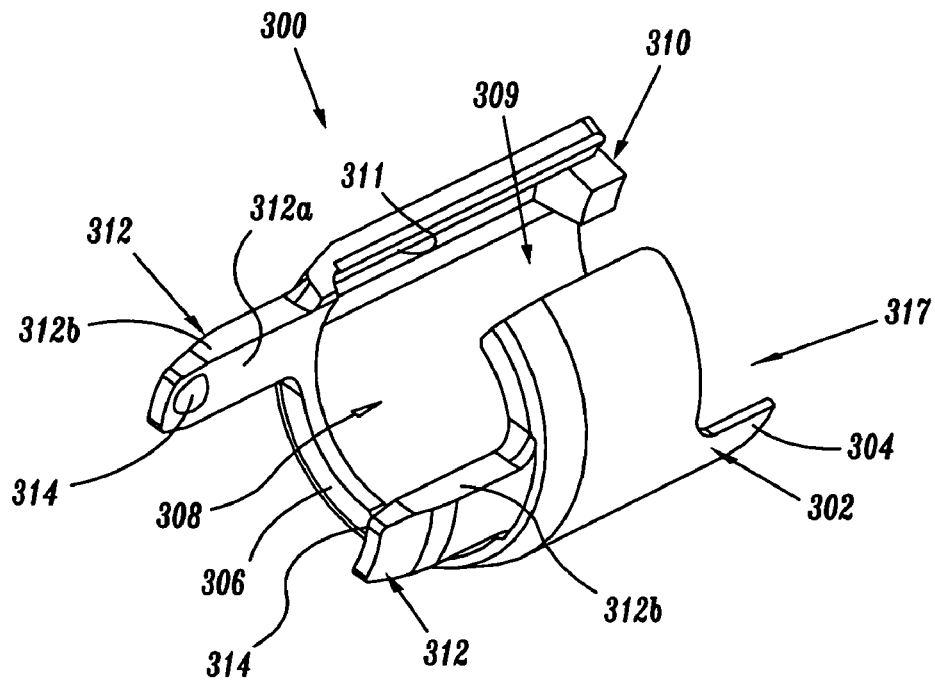
FIG. 15 is an enlarged front perspective view of a preferred locking member according to the present disclosure.
Figure 16:
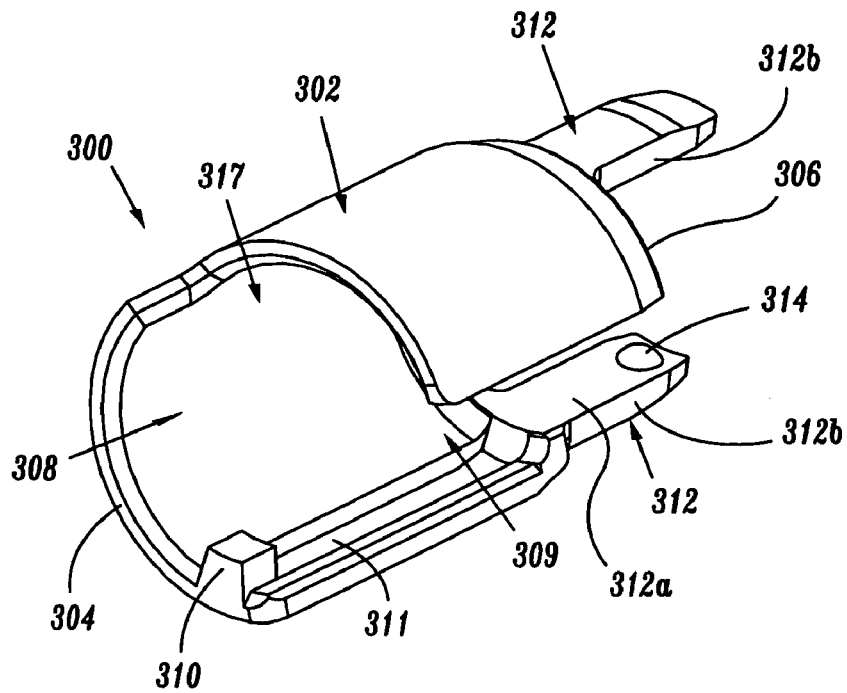
FIG. 16 is an enlarged rear perspective view of the locking member of FIG. 15.
Figure 23:
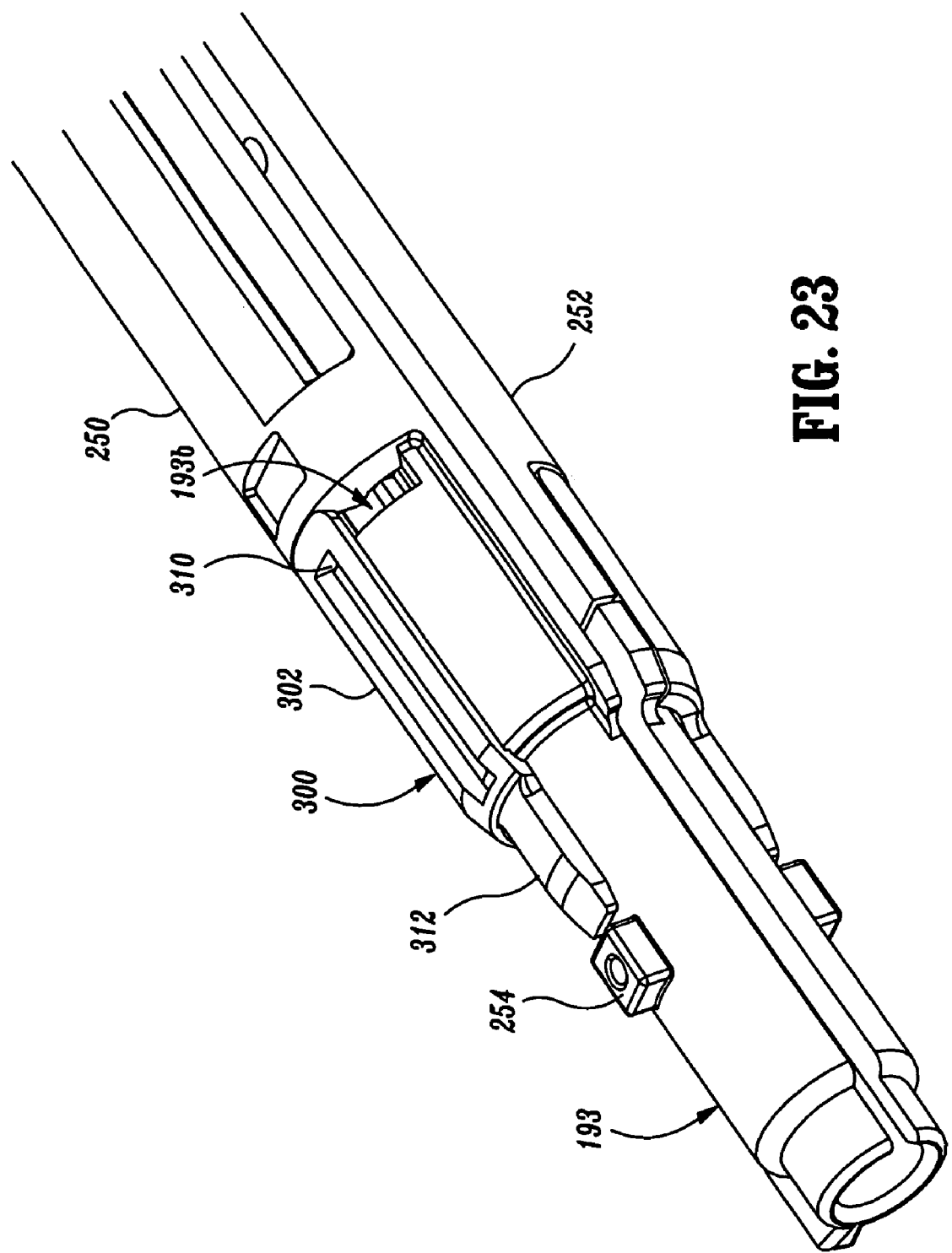
FIG. 23 is an enlarged perspective view of the proximal end of the DLU of FIGS. 6–9 illustrating the locking member of FIGS. 15–22 situated in the first position.

Turning now to FIGS. 27–32, a method of use and/or operation of locking member 300, and/or for connecting drive assembly 212 of DLU 16 to control rod 52 of elongate body 14 and for securing DLU 16 to the distal end of elongate body 14, will now be discussed. Prior to attachment, i.e., loading, of DLU 16 to elongate body 14 of stapling apparatus 10 (FIG. 27), locking member 300 is in the first position such that tooth 310 is in engagement with notch 270c of engagement section 270 of drive assembly 212 (FIGS. 23, 24 and 28). As discussed above, engagement of tooth 310 with notch 270c retains drive assembly 212 of DLU 16 in its proximal-most, locked, ready-to-load, position. To secure, attach or load DLU 16 to elongate body 14 of stapling apparatus 10, as seen in FIGS. 27 and 28, insertion tip 193 of DLU 16 is introduced longitudinally into the distal end of elongate body 14, in the direction of arrow "A", such that nubs 254 are received in channels 276d of elongate body 14 (see also FIGS. 14 and 14a). Channels 276d are defined by projections 276c extending radially inward from elongate body 14 near the distal end thereof (FIGS. 14 and 14a). During the introduction of insertion tip 193 of DLU 16, distal end 276 (FIG. 14) of control rod 52 enters porthole 274 (FIG. 12) provided at the proximal end of drive assembly 212. When insertion tip 193 has been fully inserted (FIGS. 29 and 30) into the distal end of elongate body 14, and more particularly, when nubs 254 have completely passed projections 276c, DLU 16 is rotated, in the direction of arrow "B" (FIGS. 31 and 32), such that projections 276c of elongate body 14 abut against and engage fingers 312 of locking member 300, preferably against a side surface 312b of fingers 312.

Continued rotation of DLU 16, in the direction of arrow "B", causes projections 276c of elongate body 14 to move fingers 312 and locking member 300 from the first position to the second position to thereby disengage tooth 310 from notch 270c of engagement section 270 of drive assembly 212, thereby freeing drive assembly 212 to operate in surgical stapling apparatus 10. Movement of locking member 300 from the first position to the second position attaches, secures or loads DLU 16 to or onto elongate shaft 14. With control rod 52 connected at its distal end to drive assembly 212, distal movement of control rod 52 effects distal movement of drive assembly 212 thereby moving cam rollers 286 into engagement with a cam surface (not shown) disposed within anvil assembly 20 to move/urge anvil assembly 20 toward cartridge assembly 18, to fire cartridge assembly 18, and to drive knife blade 280 (FIG. 11) through the tissue.

As can be appreciated, if locking member 300 has been inadvertently moved to the second position, prior to attempting to load DLU 16 to elongate body 14, and drive assembly 212 has prematurely moved distally from its proximal-most or ready-to-load position, locking member 300 can not return to the first position due to tooth 310 not being aligned with notch 270c and abutting against a portion of engagement section 270. In such a situation, if locking member 300 is prevented from returning to the first position, upon attempting to load DLU 16 to elongate body 14, fingers 312 of locking member 300 will abut against and/or otherwise contact projection 276c of elongate body 14 and thus prevent loading of DLU 16 to elongate body 14. Accordingly, the loading of a DLU having a drive assembly, e.g., 212, which is not in its ready-to-load position is prevented.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical stapling apparatus comprising:
   a housing;
   a handle supported by the housing; and
   a loading unit supportable on a distal end of the housing, the loading unit including:
      a housing portion including a distal end and a proximal end;
      a drive assembly slidably supported within the housing portion of the loading unit; and
      a locking member supported on the housing portion of the loading unit and being independently rotatable relative to the housing of the surgical stapling apparatus while the loading unit is being coupled to said housing of said surgical stapling apparatus, the locking member including a locking portion extending through the housing portion, the locking member being rotatably movable from a first position wherein the locking portion engages the drive assembly and maintains the drive assembly in a ready-to-load position to a second position wherein the locking portion permits movement of the drive assembly relative to the housing portion.

2. The surgical stapling apparatus of claim 1, wherein the drive assembly includes a notch and the locking member includes:
   a cuff-like body portion that at least partially surrounds the proximal end of the housing portion; and
   a tooth extending radially inward from the body portion, wherein the tooth selectively engages the notch formed in the drive assembly such that when the locking member is in the first position the tooth engages the notch of the drive assembly and maintains the drive assembly in the ready-to-load position, and when the locking member is in the second position the tooth is disengaged from the notch of the drive assembly.

3. The surgical stapling apparatus of claim 2, wherein the proximal end of the housing portion includes an annular slot formed therein for receiving the tooth of the locking member therein.

4. The surgical stapling apparatus of claim 3, wherein the locking member further includes at least one finger extending axially from a proximal end thereof, wherein when the locking member is in the first position, the finger is axially aligned with a nub extending radially outward from the proximal end of the housing portion and when the locking member is in the second position the finger is out of axial alignment with the nub of the proximal end of the housing portion.

5. The surgical stapling apparatus of claim 4, wherein the housing includes a radially inwardly extending projection and the locking member is urged from the first position to the second position by the projection, the projection acting on a side surface of the finger as the loading unit is twisted into engagement in and with the housing.

6. The surgical stapling apparatus of claim 5, wherein each finger of the locking member includes a detent projecting from an inner surface thereof for selective engagement with a complementary recess formed in an outer surface of the proximal end of the housing portion.

7. The surgical stapling apparatus of claim 6, wherein the finger of the locking member is axially aligned with the tooth.

8. The surgical stapling apparatus of claim 7, wherein the locking member includes a pair of opposed fingers extending axially from a proximal end thereof, wherein when the locking member is in the first position, one of the pair of fingers is axially aligned with the nub extending radially outward from the proximal end of the housing portion and when the locking member is in the second position the finger is out of axial alignment with the nub of the proximal end of the housing portion.

9. The surgical stapling apparatus according to claim 8, wherein the surgical stapling apparatus is a laparoscopic or endoscopic stapler.

10. The surgical stapling apparatus according to claim 9, further comprising an elongate body extending from the housing.

11. The surgical stapling apparatus according to claim 10, wherein the proximal end of the housing portion defines an insertion tip.

12. A loading unit selectively supportable on a distal end of an elongate body of a surgical stapling apparatus, the loading unit comprising:
   a housing portion including a distal end and a proximal end;
   a drive assembly slidably supported within the housing portion; and
   a locking member for maintaining a drive assembly in a ready-to-load position while the loading unit is being coupled to the elongate body of the surgical stapling apparatus, the locking member being independently rotatable relative to the housing portion from a first position to a second position, the locking member comprising:
      a cuff-like body portion that at least partially surrounds an insertion tip of the loading unit; and
      a tooth extending radially inward from the body portion, wherein the tooth selectively engages a notch formed in the drive assembly such that when the locking member is in the first position the tooth engages the notch of the drive assembly and maintains the drive assembly in the ready-to-load position, and when the locking member is in the second position the tooth is disengaged from the notch of the drive assembly.

13. The loading unit according to claim 12, wherein the proximal end of the housing portion includes an annular slot formed therein for receiving the tooth of the locking member therein.

14. The loading unit according to claim 13, wherein the locking member further includes at least one finger extending axially from a proximal end thereof, wherein when the locking member is in the first position, the finger is axially aligned with a nub extending radially outward from the proximal end of the housing portion and when the locking member is in the second position the finger is out of axial alignment with the nub of the proximal end of the housing portion.

15. The loading unit according to claim 14, wherein the locking member is urged from the first position to the second position by a radially inward extending projection provided in the elongate body of the surgical stapling apparatus, the projection acting on a side surface of the finger as the loading unit is twisted into engagement in and with the elongate body.

16. The loading unit according to claim 15, wherein each finger of the locking member includes a detent projecting from an inner surface thereof for selective engagement with a complementary recess formed in an outer surface of the proximal end of the housing portion.

17. The loading unit according to claim 16, wherein the finger of the locking member is axially aligned with the tooth.

18. The loading unit according to claim 17, wherein the locking member includes a pair of opposed fingers extending axially from a proximal end thereof, wherein when the locking member is in the first position, one of the pair of fingers is axially aligned with the nub extending radially outward from the proximal end of the housing portion and when the locking member is in the second position the finger is out of axial alignment with the nub of the proximal end of the housing portion.

19. The loading unit according to claim 18, wherein the loading unit is selectively connectable to at least one of a laparoscopic and an endoscopic stapler.

20. A loading unit selectively supportable on a distal end of an elongate body of a surgical stapling apparatus, the loading unit comprising:
   a housing portion including a distal end and a proximal end;
   a drive assembly slidably supported within the housing portion; and
   a locking member supported on the housing portion and being independently rotatable relative to the housing of the surgical stapling apparatus while the loading unit is being coupled to said housing, of said surgical stapling apparatus the locking member including a locking portion extending through the housing portion, the locking member being movable from a first position wherein the locking portion engages the drive assembly and maintains the drive assembly in a ready-to-load position to a second position wherein the locking portion permits movement of the drive assembly relative to the housing portion.

* * * * *